United States Patent
Sopp et al.

(10) Patent No.: US 7,041,067 B2
(45) Date of Patent: May 9, 2006

(54) BODY FLUID SAMPLER

(75) Inventors: John P. Sopp, White Bear Lake, MN (US); Scott T. Latterell, Minneapolis, MN (US); Paul D. Brinda, Robbinsdale, MN (US); Timothy J. Erskine, Sandy, UT (US)

(73) Assignee: InTeg, Inc., St. Paul, MN (US)

( * ) Notice: Subject to any disclaimer, the term of this patent is extended or adjusted under 35 U.S.C. 154(b) by 0 days.

(21) Appl. No.: 10/613,117

(22) Filed: Jul. 3, 2003

(65) Prior Publication Data

US 2004/0049130 A1    Mar. 11, 2004

Related U.S. Application Data

(60) Continuation of application No. 10/233,046, filed on Aug. 30, 2002, now Pat. No. 6,624,882, which is a continuation of application No. 09/723,339, filed on Nov. 27, 2000, now Pat. No. 6,614,522, which is a continuation of application No. 09/264,461, filed on Mar. 8, 1999, now Pat. No. 6,152,889, which is a division of application No. 08/706,663, filed on Sep. 6, 1996, now Pat. No. 5,879,310, which is a continuation-in-part of application No. 08/525,390, filed on Sep. 8, 1995, now abandoned, and a continuation-in-part of application No. 08/525,942, filed on Sep. 8, 1995, now Pat. No. 5,879,367.

(51) Int. Cl.
*A61B 5/00* (2006.01)
*A61B 17/14* (2006.01)
*A61B 17/32* (2006.01)
*A65D 81/00* (2006.01)

(52) U.S. Cl. .................. 600/578; 600/584; 606/182

(58) Field of Classification Search .................. 356/39
See application file for complete search history.

(56) References Cited

U.S. PATENT DOCUMENTS

| | | | |
|---|---|---|---|
| 3,123,066 | A | 3/1964 | Brumley |
| 3,136,310 | A | 6/1964 | Meltzer |
| 3,208,452 | A | 9/1965 | Stern |
| 3,338,239 | A | 8/1967 | Mausteller |
| 3,958,560 | A | 5/1976 | March |
| 4,014,321 | A | 3/1977 | March |
| 4,195,641 | A | 4/1980 | Johnes et al. |
| 4,200,110 | A | 4/1980 | Peterson et al. |
| 4,407,290 | A | 10/1983 | Wilber |

(Continued)

FOREIGN PATENT DOCUMENTS

DE    37 08 031 A1    11/1987

(Continued)

OTHER PUBLICATIONS

Moatti-Sirat, D. et al., "Towards Continuous Glucose Monitoring: In Vivo Evaluation of Miniaturized Glucose Sensor Implanted for Several Days in Rat Subcutaneous Tissue", *Diabetologia*, vol. 35, pp. 224-230 (1992).

(Continued)

*Primary Examiner*—Michael P. Stafira

(57) ABSTRACT

A sampling apparatus for sampling body fluid includes a sampler having an external geometry selected to mate with an internal geometry of a testing apparatus such that the sampler may be inserted within the testing apparatus in a predetermined alignment—and with a sampling location positioned accurately within a light path for detecting an amount of a desired constituent within fluid collected by the sampler.

5 Claims, 28 Drawing Sheets

U.S. PATENT DOCUMENTS

| | | | |
|---|---|---|---|
| 4,489,974 A | 12/1984 | Warhol | |
| 4,517,978 A | 5/1985 | Levin et al. | |
| 4,407,290 A | 10/1986 | Wilber | |
| 4,622,974 A | 11/1986 | Coleman et al. | |
| 4,637,403 A | 1/1987 | Garcia et al. | |
| 4,648,408 A | 3/1987 | Hutcheson et al. | |
| 4,655,225 A | 4/1987 | Dahne et al. | |
| 4,660,971 A | 4/1987 | Sage et al. | |
| 4,685,463 A | 8/1987 | Williams | |
| 4,703,756 A | 11/1987 | Gough et al. | |
| 4,704,029 A | 11/1987 | Van Heuvelen | |
| 4,730,622 A | 3/1988 | Cohen | |
| 4,750,830 A | 6/1988 | Lee | |
| 4,805,623 A | 2/1989 | Jobsis | |
| 4,873,993 A | 10/1989 | Meserol et al. | |
| 4,882,492 A | 11/1989 | Schlager | |
| 4,883,068 A | 11/1989 | Dechow | |
| 4,901,728 A | 2/1990 | Hutchinson | |
| 4,953,552 A | 9/1990 | DeMarzo | |
| 4,954,318 A | 9/1990 | Yafuso et al. | |
| 4,960,467 A | 10/1990 | Peck | |
| 4,981,779 A | 1/1991 | Wagner | |
| 5,002,054 A | 3/1991 | Ash et al. | |
| 5,014,718 A | 5/1991 | Mitchen | |
| 5,026,388 A | 6/1991 | Ingalz | |
| 5,029,583 A | 7/1991 | Meserol et al. | |
| 5,035,704 A | 7/1991 | Lambert et al. | |
| 5,054,499 A | 10/1991 | Swierczek | |
| 5,066,859 A | 11/1991 | Karkar et al. | |
| 5,070,886 A | 12/1991 | Mitchen et al. | |
| 5,079,421 A | 1/1992 | Knudson et al. | |
| 5,115,133 A | 5/1992 | Knudson | |
| 5,146,091 A | 9/1992 | Knudson | |
| 5,179,951 A | 1/1993 | Knudson | |
| 5,201,324 A | 4/1993 | Swierczek | |
| 5,231,993 A | 8/1993 | Haber et al. | |
| 5,320,607 A | 6/1994 | Ishibashi | |
| 5,368,047 A | 11/1994 | Suzuki et al. | |
| 5,437,841 A | 8/1995 | Balmer | |
| 5,458,140 A | 10/1995 | Eppstein et al. | |
| 5,470,757 A | 11/1995 | Gagnon et al. | |
| 5,582,184 A * | 12/1996 | Erickson et al. | 600/576 |
| 5,682,233 A | 10/1997 | Brinda | |
| 5,746,217 A | 5/1998 | Erickson et al. | |
| 5,820,570 A | 10/1998 | Erickson et al. | |
| 5,879,310 A * | 3/1999 | Sopp et al. | 600/578 |
| 5,879,367 A | 3/1999 | Latterell et al. | |
| 6,624,882 B1 * | 9/2003 | Sopp et al. | 356/39 |

FOREIGN PATENT DOCUMENTS

| | | |
|---|---|---|
| EP | 0 160 768 A1 | 11/1985 |
| EP | 0 199 484 A2 | 10/1986 |
| EP | 0 212 906 A2 | 3/1987 |
| EP | 0 250 257 A1 | 12/1987 |
| EP | 0 453 283 A1 | 10/1991 |
| EP | 0 582 226 A1 | 2/1994 |
| GB | 2 033 575 A | 5/1980 |
| WO | WO 85/04089 | 9/1985 |
| WO | WO 88/00812 | 2/1988 |
| WO | WO 91/18548 | 12/1991 |
| WO | WO 95/10223 | 4/1995 |

OTHER PUBLICATIONS

Petersen, L. et al., "Microdialysis of the Interstitial Water Space in Human Skin *In Vivo*: Quantitative Measurement of Cutaneous Glucose Concentrations," J Invest Dermatol, vol. 99, No. 3, pp. 357-360 (Sep. 1992).

Turner, A. et al., "Diabetes Mellitus: Biosensors for Research and Management," *Biosensors*, vol. 1, pp. 85-115 (1985).

Wiig. H, "Evaluation of Methodologies for Measurement of Interstitial Fluid Pressure (Pi): Physiological Implications of Recent Pi Data," Crit Rev Biomed Eng, vol. 18, No. 1, pp. 27-54 (1990).

Wolfson, Jr., S. et al., "Glucose Concentration at Possible Sensor Tissue Implant Sites," Diabetes, vol. 5, No. 3, pp. 162-165 (May-Jun. 1982).

Kayashima, S. et al., "New Noninvasive Transcutaneous Approach to Blood Glucose Monitoring: Successful Glucose Monitoring on Human 75 g OGTT with Novel Sampling Chamber," *IEEE Transactions on Biomedical Engineering*, vol. 38, No. 8, pp. 752-757 (Aug. 1991).

Kayashima S. et al., Suction Effusion Fluid From Skin and Constituent Analysis: New Candidate for Interstitial Fluid, *Am J. Physiol* (United States) Nov. 1992, 263 (5 Pt 2), pp. H1623-H1627.

Khstala, U., "Suction Blister Device for Separation of Viable Epidermis from Dermis," *Journal of Investigative Dermatology*, vol. 50, No. 2, pp. 120-137 (1968).

Korthius, R. et al., "Method for Sampling Interstitial Fluid" from book entitled *Microcirculatory Technology*, edited by D. H. Baker et el., Academic Press, Chapter 21, pp. 326-327 (1986).

Mendelson, Y. et al., "Blood Glucose Measurement by Multiple Attenuated Total Reflection and Infrared Absorption Spectroscopy," *IEEE. Transactions on Biomedical Engineering*, vol. 37, No. 5, pp. 458-465 (May 1990).

Gelman Science brochure, p. 60 (1993) showing Nylaflo, Catalog P/N 32378.

Gilanyi, M. et al., "Ion Concentrations in Subcutaneous Interstitial Fluid: Measured Versus Expected Values," *Am. J. Physiol*. (United States) Sep. 1988, 255 (3 Pt 2) pp. F513-F519.

Ginsberg, B. "An Overview of Minimally Invasive Technologies", *Clinical Chemistry*, vol. 38, No. 9, pp. 1596-1600 (1992).

"Glucose Sensors" and "Like An Injection" sections on p. 26 of Diabetes Forecast, May 1993.

Janle—Swain, E. et al., "Use of Capillary Filtrate Collector for Monitoring Glucose in Diabetics," *Trans. Am. Artif. Intern. Organs*, vol. XXXIII, pp. 336-340 (1987).

Arnold, M. et al., "Determination of Physiological Levels of Glucose in an Aqueous Matrix with Digitally Filtered Fourier Transform Near-Infrared Spectra," *Anal. Chem*., vol. 62, pp. 1457-1464 (1990).

Ash, S. et al., "Subcutaneous Capillary Filtrate Collector for Measurement of Blood Glucose," *ASAIO Journal*, vol. 38, pp. M416-M420 (1992).

Ash, S.et al., "A Subcutaneous Capillary Filtrate Collector for Measurement of Blood Chemistries," *ASAIO Journal*, vol. 39, pp. M699-M705 (1993).

Brace, R. et al., "Reevaluation of the Needle Method for Measuring Interstitial Fluid Pressure," *Am J. Physiol*., vol. 229, No. 3, pp. 603-607 (Sep. 1975).

DuPuy, N. et al., "Quantitative Analysis of Aqueous Solutions by FTIR Spectroscopy of Dry Extract", SPIE, vol. 1575, 8th International Conference on Fourier Transform Spectroscopy, pp. 501-502 (1991).

* cited by examiner

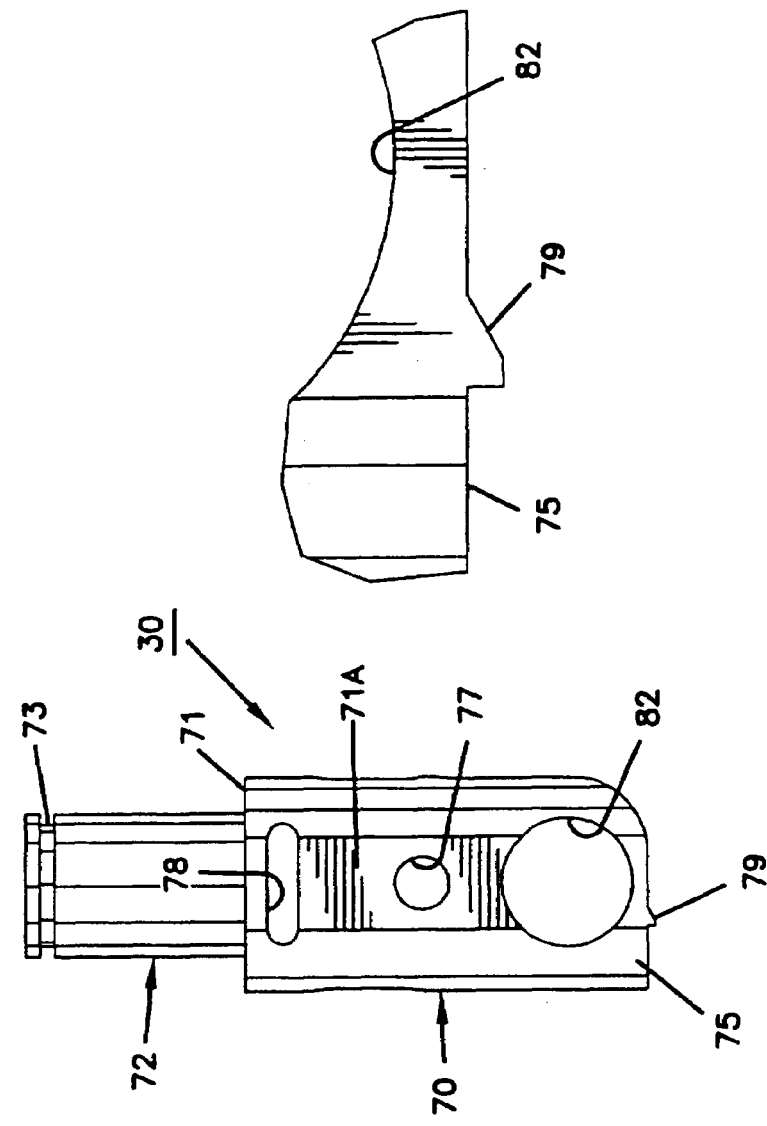
FIG. 8A
FIG. 8
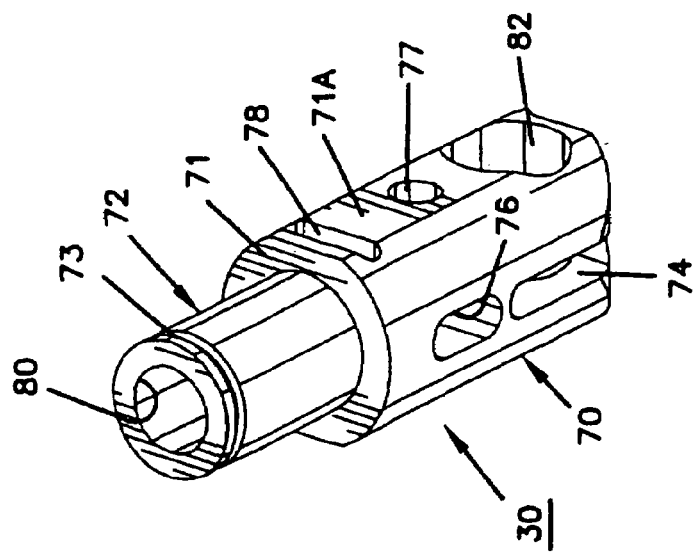
FIG. 7

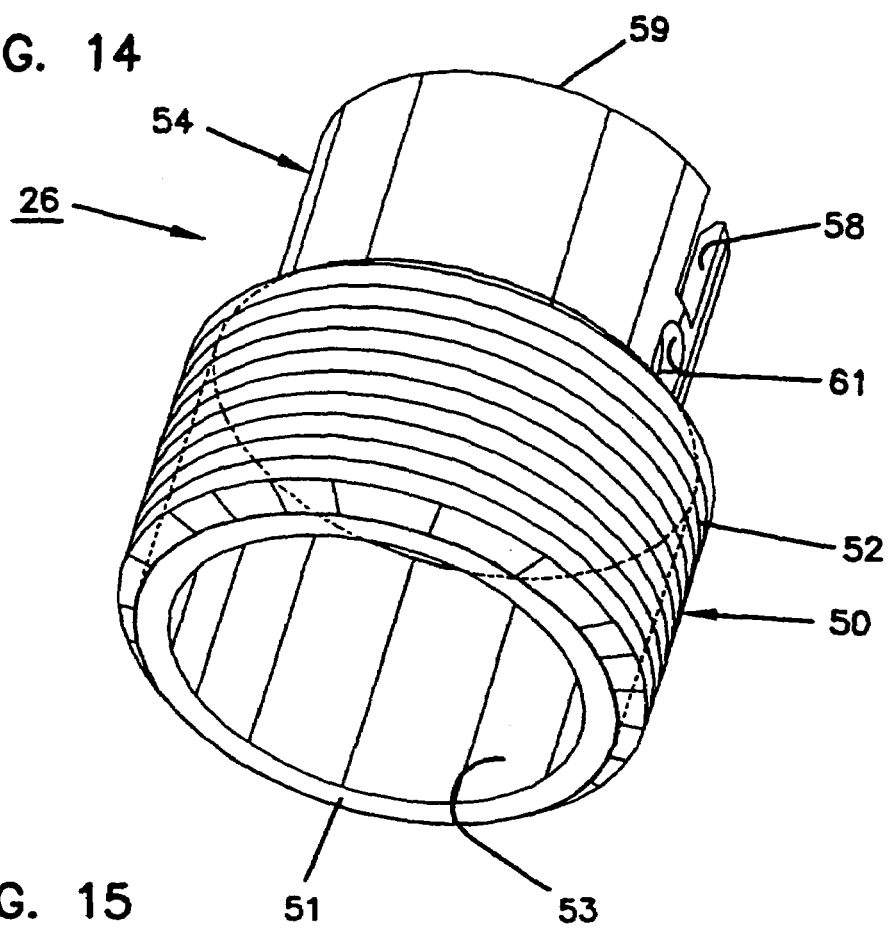
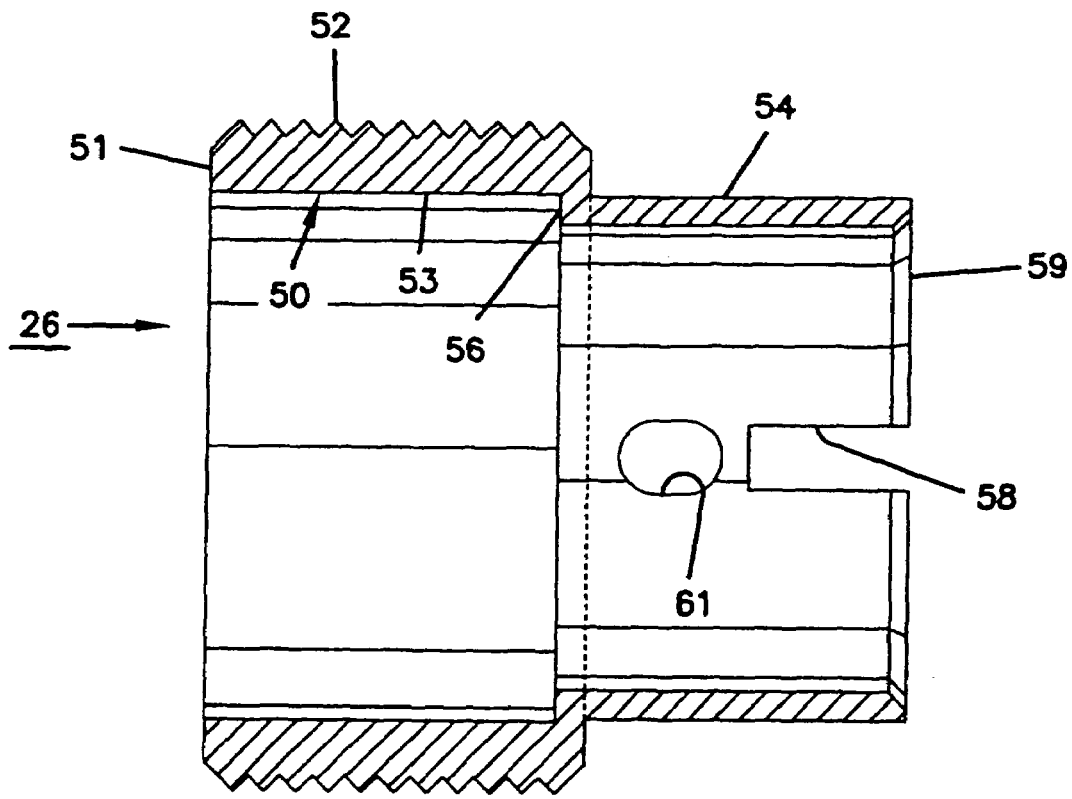

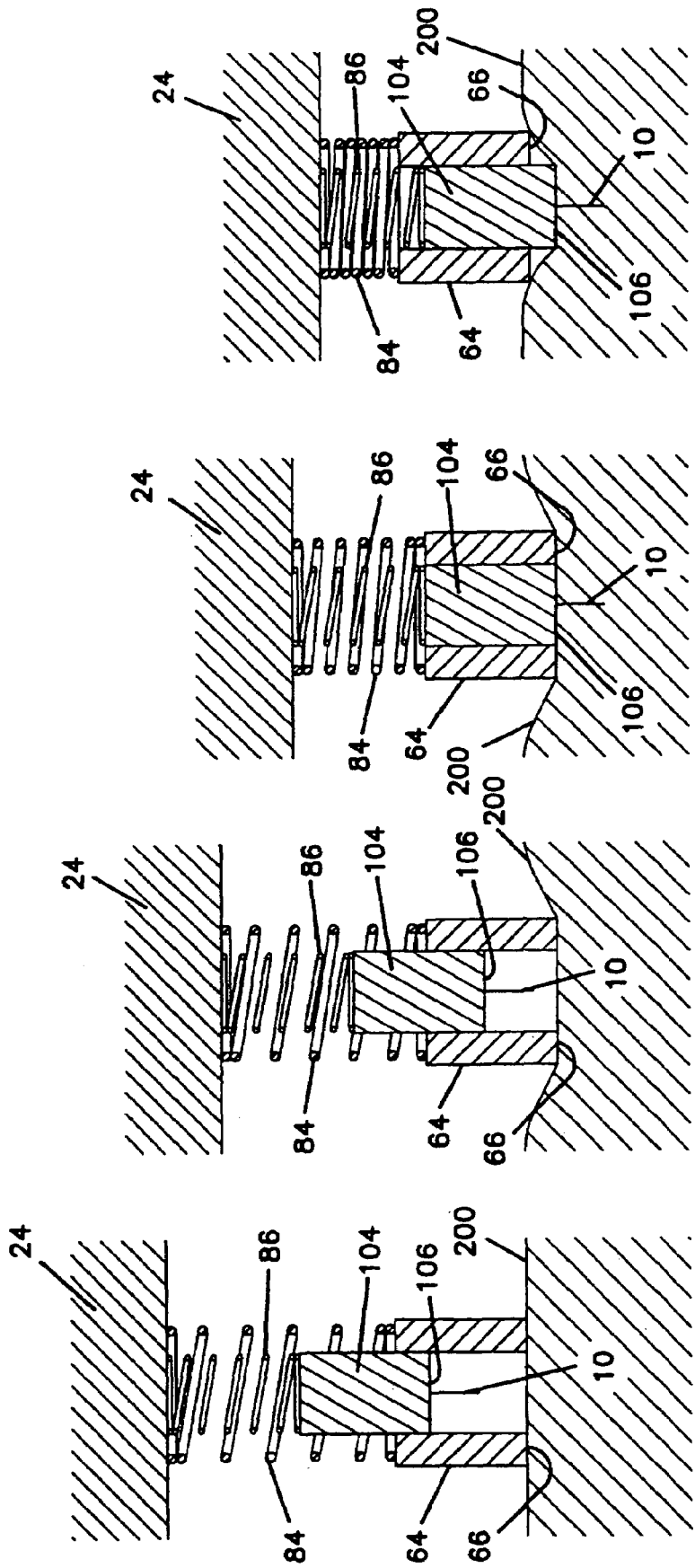

BODY FLUID SAMPLER

I. CROSS-REFERENCE TO RELATED APPLICATION

This application is a continuing application of U.S. patent application Ser. No. 10/233,046 filed Aug. 30, 2002 now U.S. Pat. No. 6,624,882 which is a continuing application of U.S. patent application Ser. No. 09/723,339, filed on Nov. 27, 2000 now U.S. Pat. No. 6,614,522, which is a continuing application of U.S. patent application Ser. No. 09/264,461, filed Mar. 8, 1999, now U.S. Pat. No. 6,152,889 which issued on Nov. 28, 2002, which is a divisional of U.S. patent application Ser. No. 08/706,663, filed on Sep. 6, 1996, now U.S. Pat. No. 5,879,310 which issued on Mar. 9, 1999, which is a continuation-in-part of U.S. patent application Ser. No. 08/525,390 filed Sep. 8, 1995, now abandoned, and a continuation-in-part of U.S. patent application Ser. No. 08/525,942 filed Sep. 8, 1995, now U.S. Pat. No. 5,879,367 which issued on Mar. 9, 1999, which application(s) and patents are incorporated herein by reference.

II. BACKGROUND OF THE INVENTION

1. Field of the Invention

This invention pertains to an apparatus for testing body fluid constituents. More particularly, this invention pertains to a sampler for use in collecting body fluids such as interstitial fluid.

2. Description of the Prior Art

In the prior art, there are numerous examples of apparatus for testing and determining the level of constituents in human blood. A great deal of attention has been directed to the development of techniques and apparatus for measuring blood glucose.

As noted in commonly assigned and co-pending U.S. patent application Ser. Nos. 08/321,305 and 08/136,304 (corresponding to PCT International Publication No. WO95/10223 published Apr. 20, 1995 on International Application No. PCT/US94/11580 and incorporated herein by reference), the determination of the level of a constituent of blood can be achieved by measuring the level of that constituent in other body fluids such as interstitial fluid. The aforementioned patent applications and international publication disclose a method and apparatus for a minimally invasive technique for collecting a sample of interstitial fluid through use of an extremely small needle which penetrates into the dermal layer of the skin in order to collect a low blood or blood-free sample of interstitial fluid. The collected interstitial fluid can then be analyzed for a determination of the level of constituents within the fluid. For example, the collected interstitial fluid can be analyzed for an amount of glucose with the determined amount being representative of the amount of glucose contained within the patient's blood.

The aforementioned applications and international publication disclose the use of a ring (item 60 in FIG. 6 of the application) which surrounds the needle to create a pressure area on the patient's skin. It is believed this leads to an increase in the amount of interstitial fluid being collected.

In the collection of interstitial fluid, it is desirable to increase the speed at which a sample is collected. In the absence of mechanical or other assistance, the rate at which interstitial fluid is collected through a small diameter tube or needle is very slow. Preferably, patients utilizing such equipment for home use will be provided with a system which collects interstitial fluid at a rapid pace to ensure that a patient does not remove the needle too early in its application. Also, it is important to provide for techniques to increase a volume of interstitial fluid being collected through a needle.

When collecting any body fluid through use of a needle, it is important that the needle be a disposable item in order to prevent re-use of the needle. Such re-use can result in the transmission of disease. Where the apparatus is to be used in a patient's home by the patient, the apparatus should be simple to use and with the needle incorporated in a disposable item. Since the needle is incorporated in a disposable item, it is important that the disposable item be amenable to low-cost manufacture. Also, in order to test the interstitial fluid, the interstitial fluid collection mechanism must be coupled with an analytic mechanism for analyzing the collected fluid. Where such a device is to be used in home by low-skilled patients, it is important that the sampler and the analytic portion of the device be mutually configured to ensure that the sampler is coupled to the apparatus in a repeatable and reliable manner to minimize errors resulting from use of the apparatus by untrained patients.

III. SUMMARY OF THE INVENTION

According to a preferred embodiment of the present invention, a sampler is disclosed for use in a body fluid collection apparatus where the collection apparatus has a light source for generating a testing light and a light detector for detecting light. The light source and the detector are contained within the apparatus in a predetermined alignment to define a light path between the source and the detector. The apparatus further includes an opening of predetermined geometry to define an access to the light path. The sampler includes a main body having a handle and a sample end. The sample end has an external mating geometry which mates with the predetermined geometry of the opening of the apparatus. Therefore, the sample end can be inserted into the opening in a predetermined alignment such that the sampler may be repeatably inserted within the opening in the predetermined alignment with a sample location of the sample end positioned within the light path. A body fluid collection apparatus is carried on the sampler. The body fluid collection apparatus includes a needle sized to protrude beyond the housing. The needle protrudes a distance selected for the needle to penetrate into a body fluid-laden skin layer when the housing is urged against the skin layer by the user. An absorbent medium is carried on the sampler in fluid flow communication with the needle for body fluid to flow from the needle onto the medium. The medium is positioned at the sample location.

IV. BRIEF DESCRIPTION OF THE DRAWINGS

FIG. 7 is a perspective view of an optics housing for use in the apparatus of FIG. 1;

FIG. 8 is a side elevation view of the housing of FIG. 7;

FIG. 8A is an enlarged view of a bottom portion of the view of FIG. 8;

FIG. 14 is a perspective view of a collar for use in the apparatus of FIG. 1;

FIG. 15 is a sectional view of the collar of FIG. 14;

FIG. 28 is a schematic representation showing the apparatus of FIG. 1 placed against a patient's skin;

FIG. 29 is the view of FIG. 28 showing initial forcing of the apparatus against the patient's skin;

FIG. 30 is the view of FIG. 28 showing urging of the apparatus against the, patient's skin with penetration of a needle into the patient's skin layer and with a piston aligned with a pressure ring;

FIG. 31 is the view of FIG. 28 with the piston protruding beyond the pressure ring;

V. DESCRIPTION OF THE PREFERRED EMBODIMENT

Figure 1:
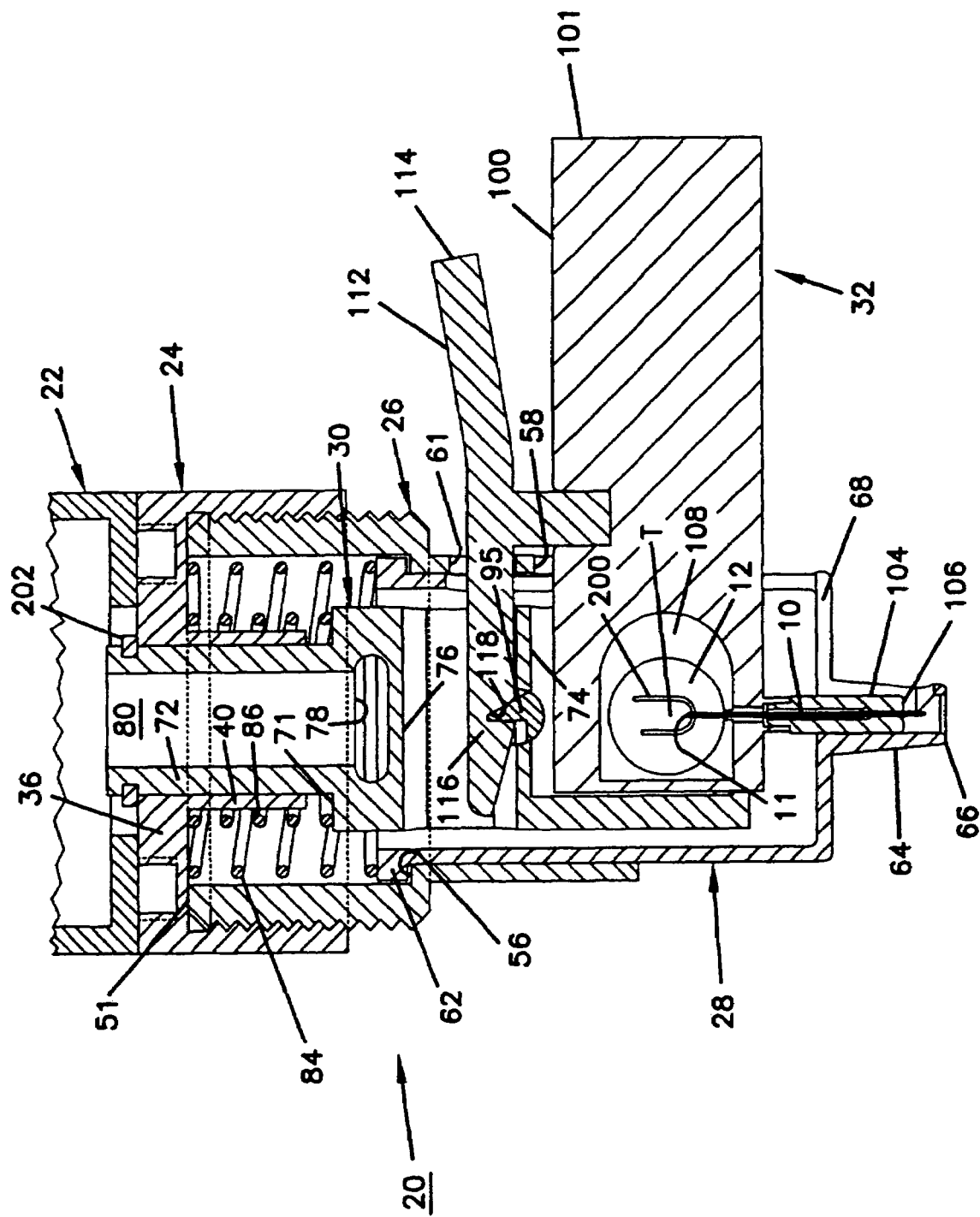
FIG. 1 is a cross-sectional elevation view of an interstitial fluid apparatus showing a sampler contained within the apparatus in a retracted position.

With reference now to the various drawing figures in which identical elements are numbered identically throughout, a description of the preferred embodiment of the present invention will be shown. While the invention will be described with reference to an apparatus for collecting interstitial fluid to test for glucose within the interstitial fluid, it will be appreciated that the apparatus can be used for testing any body constituent which may be contained within interstitial fluid.

In a preferred embodiment, the apparatus is disclosed with reference to use of a penetrating needle and an absorbing membrane such as that shown and described in U.S. patent application Ser. Nos. 08/321,305 and 08/136,304 (and corresponding PCT International Publication No. WP 95/10223, dated Apr. 20, 1995 on International Application No. PCT/US94/11580, incorporated herein by reference). With reference to FIGS. 16–20 of that application (showing a representative embodiment of the invention shown in that application), a needle 214' is surrounded and maintained in fixed relative position by a ring 202'. The ring is placed against a patient's skin in order to define a pressurized area on the patient's skin as the needle 214' penetrates into the skin. The needle is sized to be about 28 to 32 gauge (i.e., 0.36 mm outside diameter to 0.23 mm outside diameter) with an anticipated preferred size of about 30 gauge. The needle is made as small as possible to provide a minimally intrusive and painless insertion into the skin. The needle is sized to penetrate into the dermis for a variety of reasons as best disclosed in the aforementioned application including low pain and the collection of low blood interstitial fluid for subsequent testing. An absorbent membrane 210' is placed in fluid flow communication with the needle 214' such that interstitial fluid which flows through the needle 214' is deposited on the membrane 210' as a spot available for subsequent testing with light (visible or non-visible spectrum). The amount of absorption of various wavelengths of the light indicates the concentration of constituents for testing such as glucose or the like.

The present invention pertains to a testing apparatus which includes a needle 10 disposed in fluid flow communication with an absorbent membrane 12 both in accordance with the teachings of the aforementioned PCT International Publication No. WO95/10223.

A. First Described Embodiment

The present invention is directed to an apparatus 1–6) for collecting and testing interstitial fluid. The apparatus 20 includes a main housing 22 (shown in FIGS. 1 and 2 only) coupled to a base 24. The apparatus 20 further includes a collar 26 secured to the base 24. A shell 28 is contained within the collar 26. An optics housing 30 is contained within the shell 28. Finally, a sampler 32 is provided to be received within the optics housing 30. Each of base 24, collar 26, shell 28, optics housing 30 and sampler 32 will be separately described.

Figure 2:
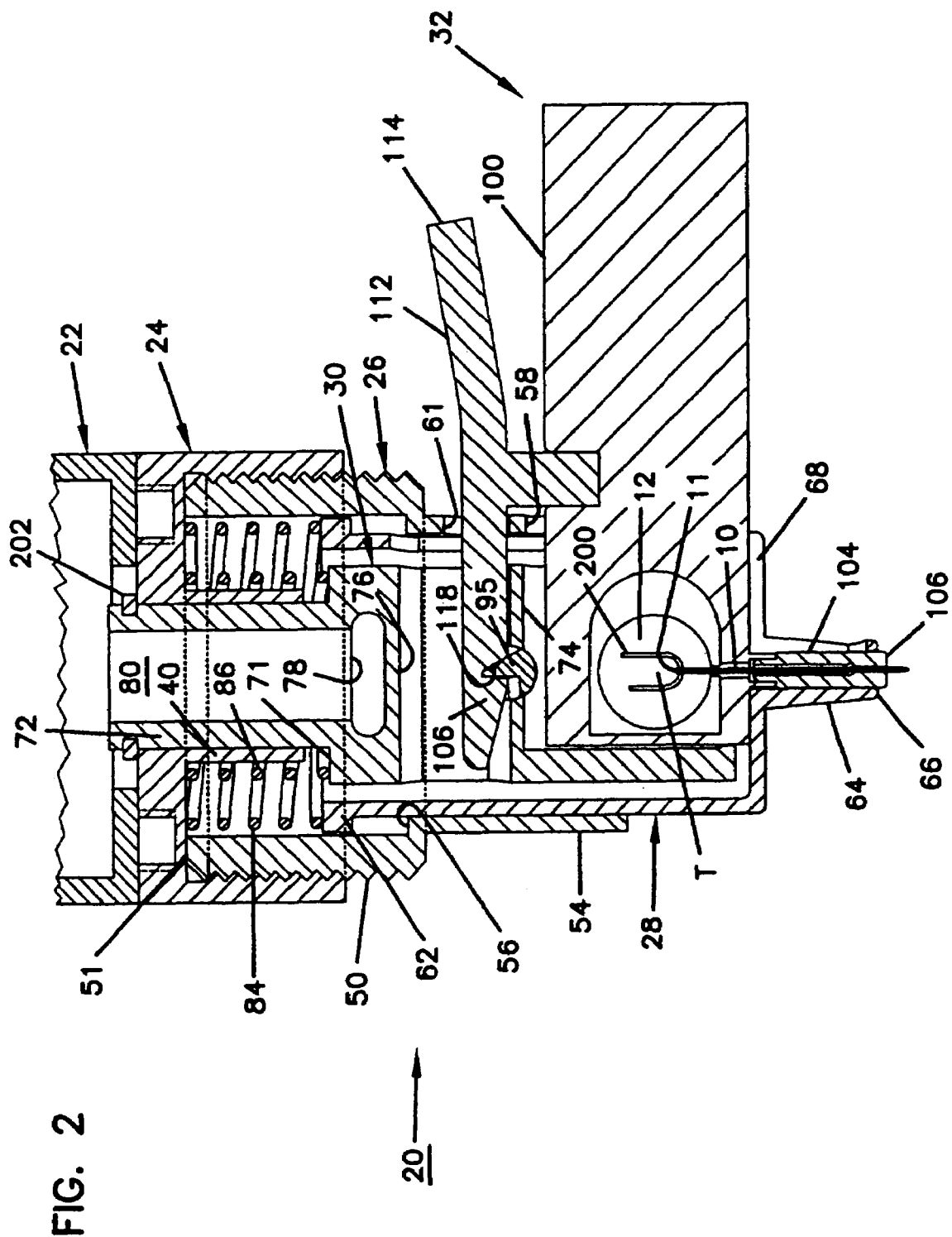
FIG. 2 is the view of FIG. 1 with the apparatus shown in an extended position.
Figure 3:
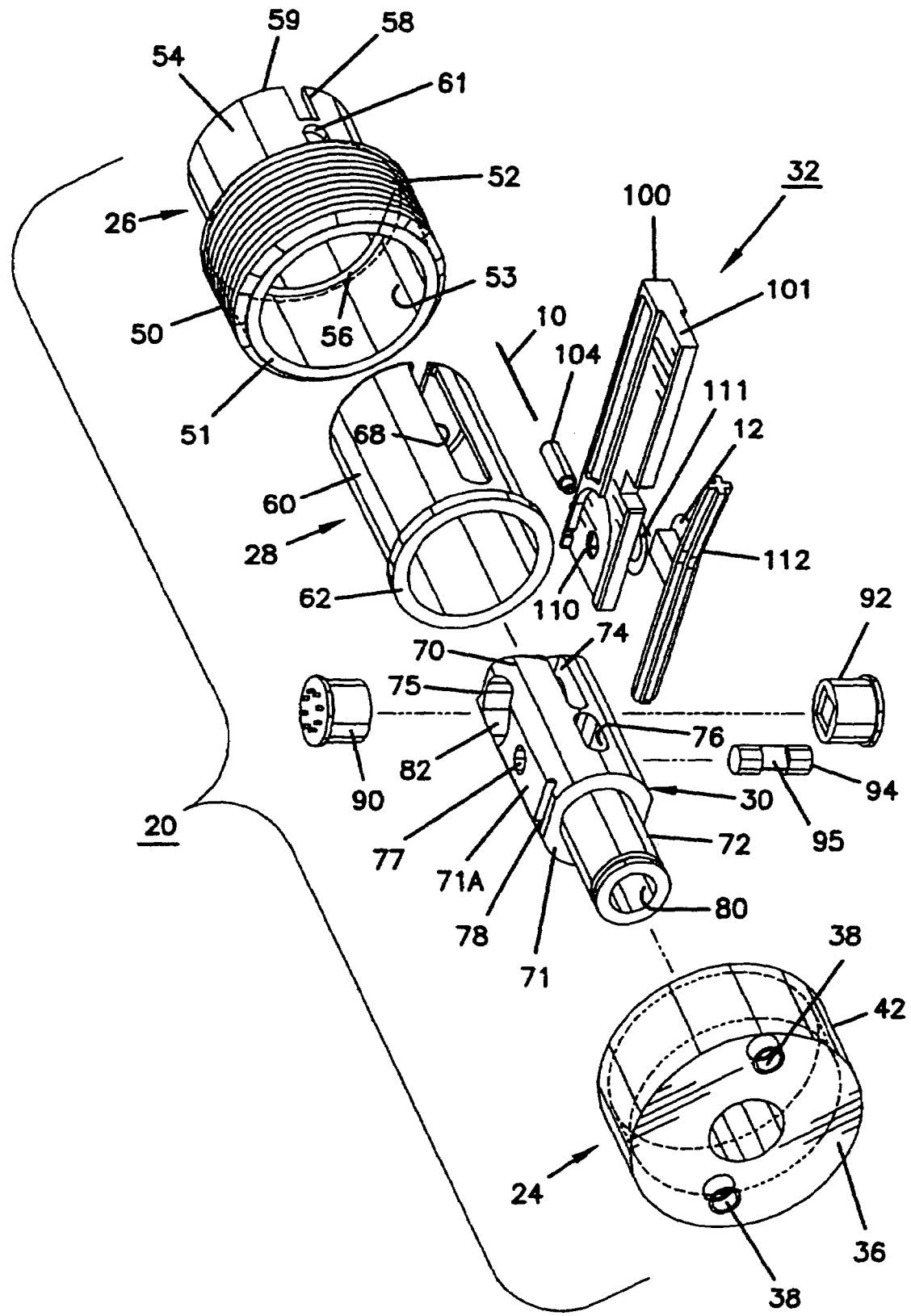
FIG. 3 is a perspective exploded view of the apparatus of FIG. 1.
Figure 4:
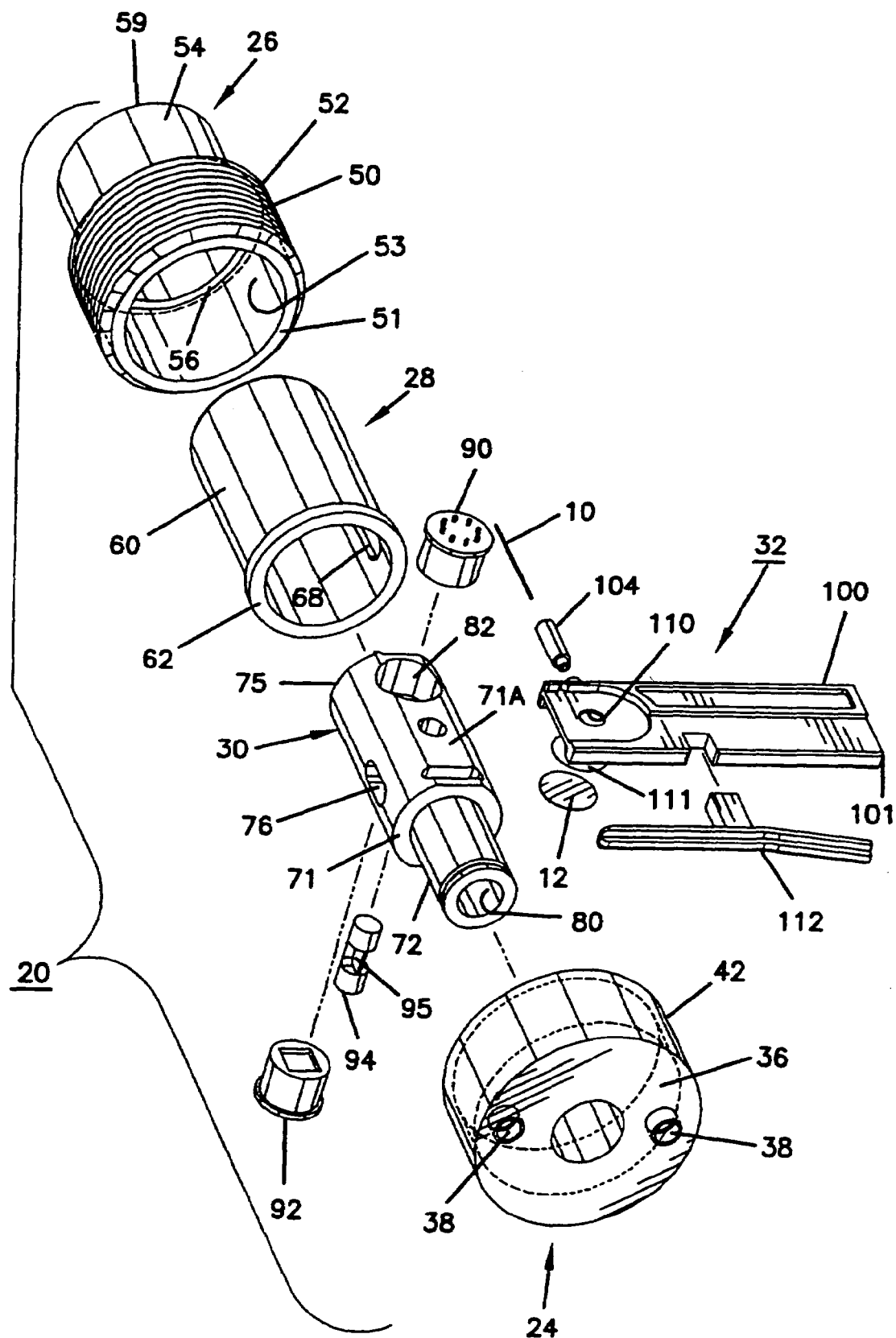
FIG. 4 is the view of FIG. 3 rotated 90° to the right of the view of FIG. 3.
Figure 5:
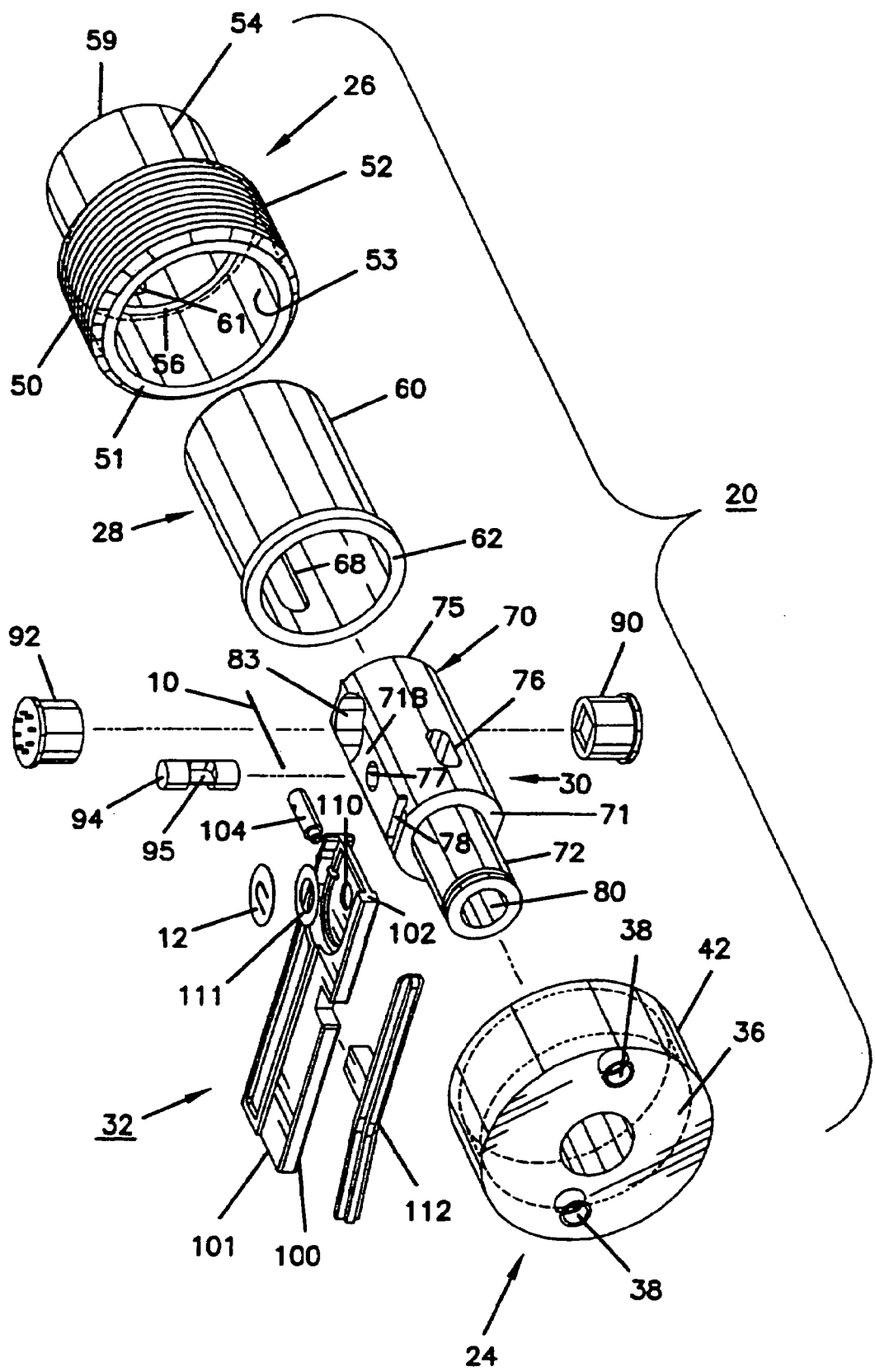
FIG. 5 is the view of FIG. 4 rotated 90° to the right of FIG. 4.
Figure 6:
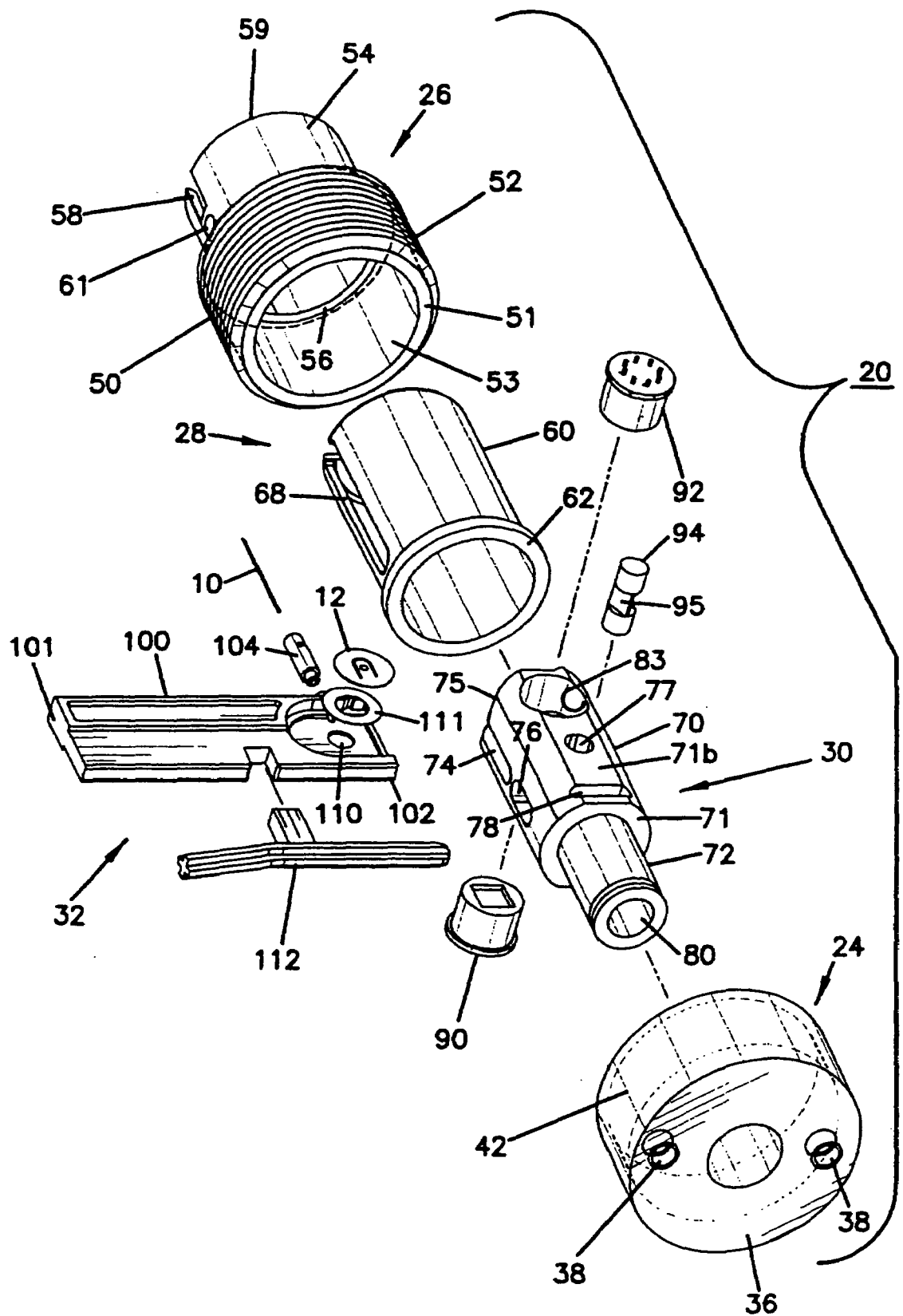
FIG. 6 is the view of FIG. 5 rotated 90° to the right of FIG. 5.
Figure 11:
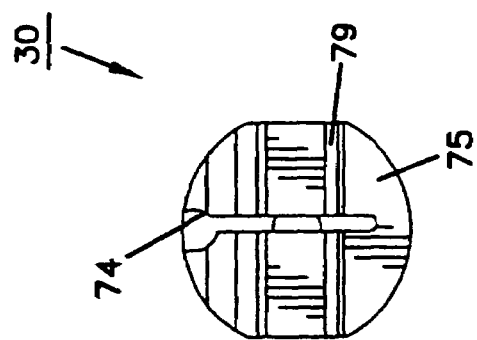
FIG. 11 is a bottom plan view of the housing of FIG. 7.
Figure 10:
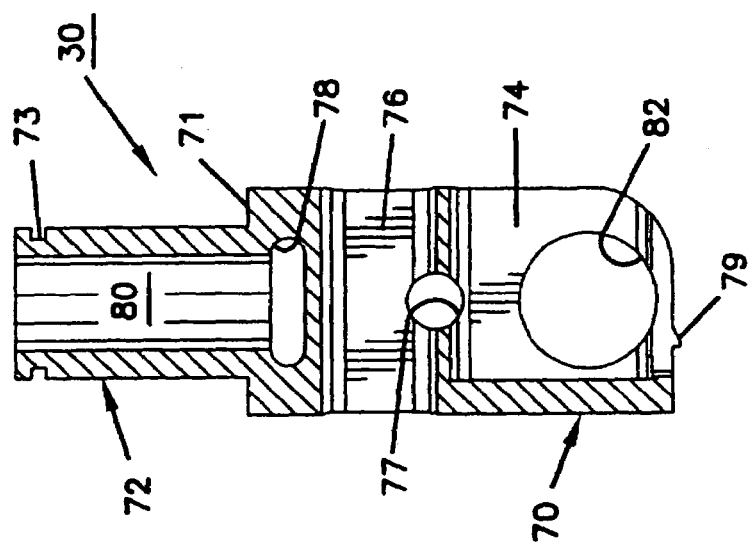
FIG. 10 is a view taken along line 10—10 of FIG. 9.
Figure 9:
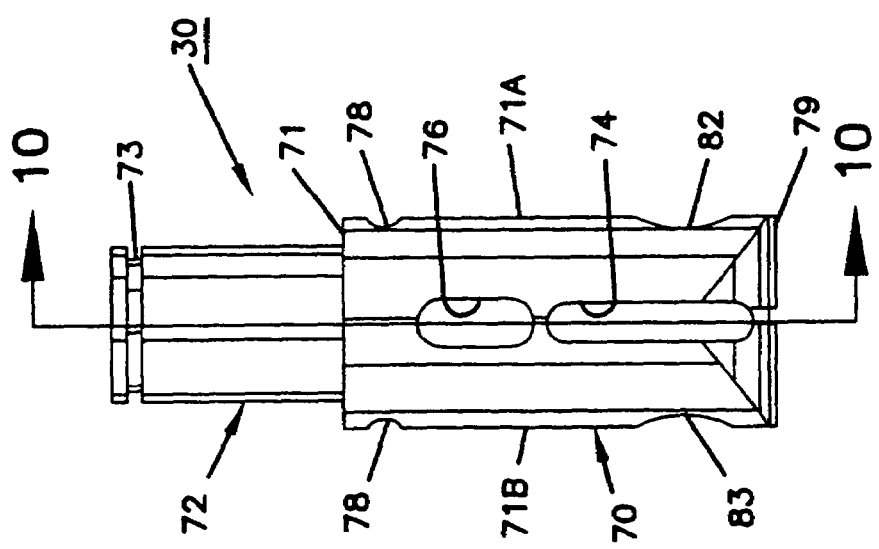
FIG. 9 is a side elevation view of the housing of FIG. 7 rotated 90° from the vies of FIG. 8.

Main housing 22 is shown only in section in FIGS. 1 and 2. Main housing 22 is sized to be gripped by a patient such that the apparatus 20 may be urged against the patient's skin for purpose of collecting interstitial fluid as will be described. In addition to constituting a handle which can be grasped by the patient, the main housing 22 will contain electronics and the like for generating power for a light source as will be-described and for analyzing signals from a light detector (as will be described) in order to calculate the level of constituents, such as blood glucose, contained within a sample of interstitial fluid. Such electronics are not shown but it will be appreciated that such electronics are well within the skill of the art. Examples of circuits for analyzing sampling light are described in commonly assigned U.S. Pat. No. 5,115,133 to Knudson dated May 19, 1992 and the aforementioned International Publication No. WO95/10223.

Figure 16:
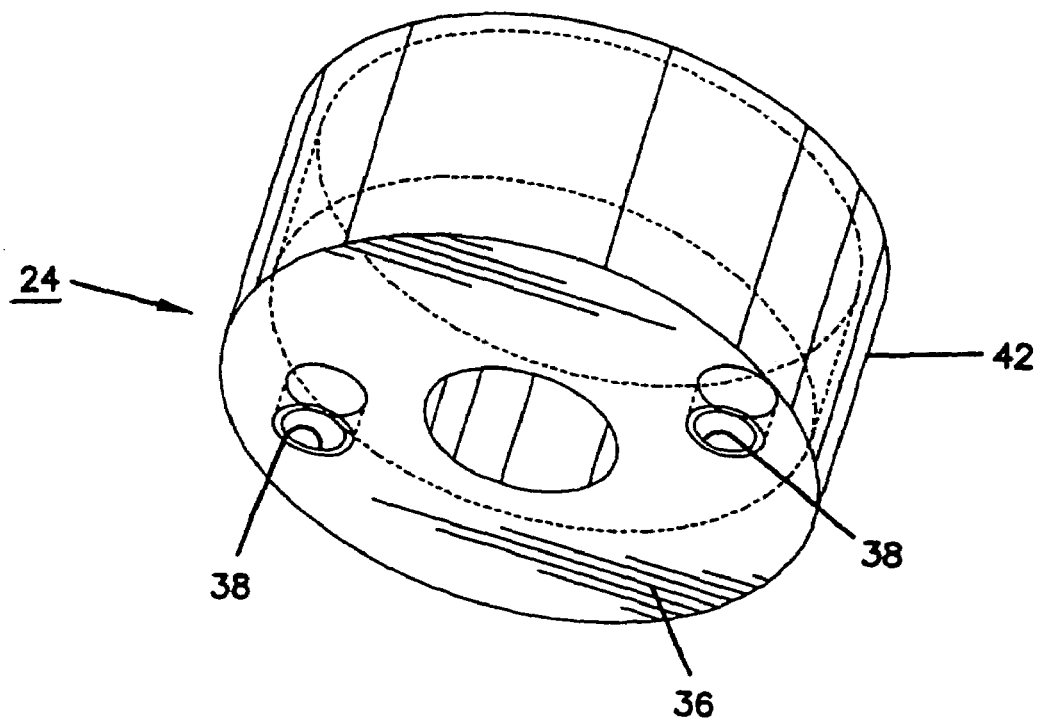
FIG. 16 is a perspective view of a base for use in the apparatus of FIG. 1.
Figure 17:
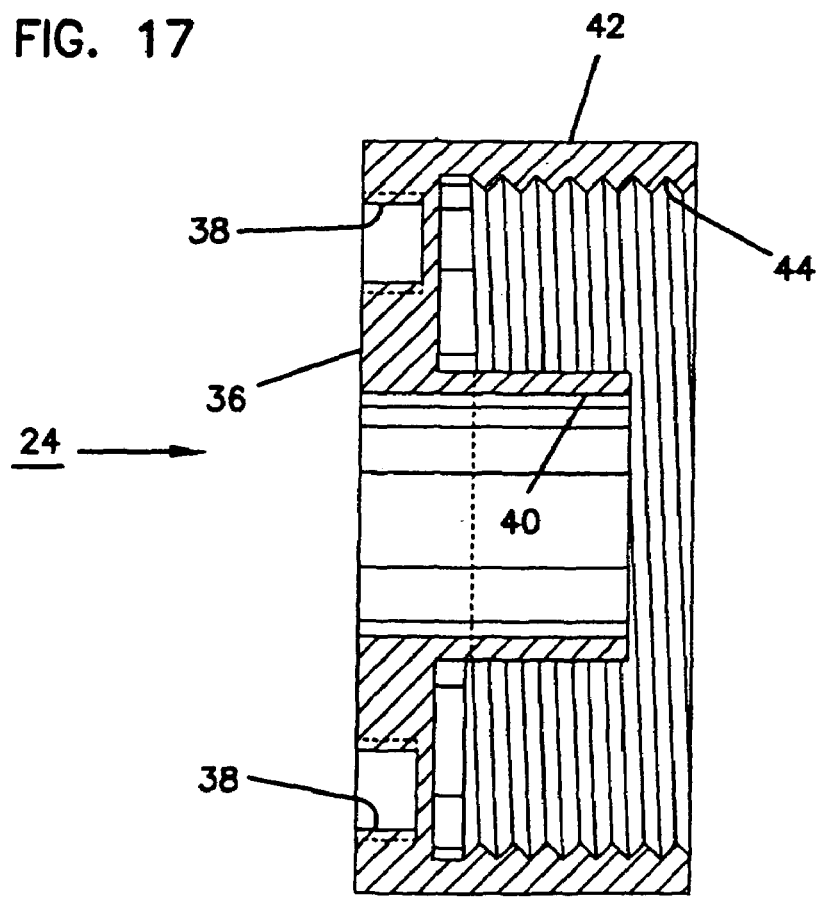
FIG. 17 is a sectional view of the base of FIG. 16.

The base 24 is separately shown in FIGS. 16 and 17. Base 24 is substantially cylindrical and is provided with an end plate 36 having holes 38 extending at least partially therethrough with the holes 38 sized to receive any suitable fastening means such as bolts or the like for fastening of the end plate 36 to the main housing 22. The base 24 further includes an inner hollow cylinder 40 extending from plate 36 with the inner cylinder 40 being coaxial with an outer cylinder 42 of the base 24. Outer cylinder 42 has a threaded inner surface 44.

The collar 26 is separately shown in FIGS. 14 and 15. The collar 26 includes an enlarged cylindrical portion 50 sized to be received within base 24 and with an end 51 abutting the end plate 36 of base 24. An outer wall 52 is threaded to mate with the internal threading 44 of base 24. An inner wall 53 of cylindrical portion 50 remains spaced from inner cylinder 40 to define a void for receiving springs as will be described (and as shown in FIGS. 1–2). The collar 26 also includes a reduced diameter portion 54 with the reduced diameter portion 54 and the enlarged diameter portion 50 connected at an annular stop surface 56 shown in FIG. 15. For purposes that will become apparent, the reduced diameter portion 54 includes a slot 58 at an end 59 of portion 54. Linearly aligned with slot 58 is a hole 61.

Figure 12:
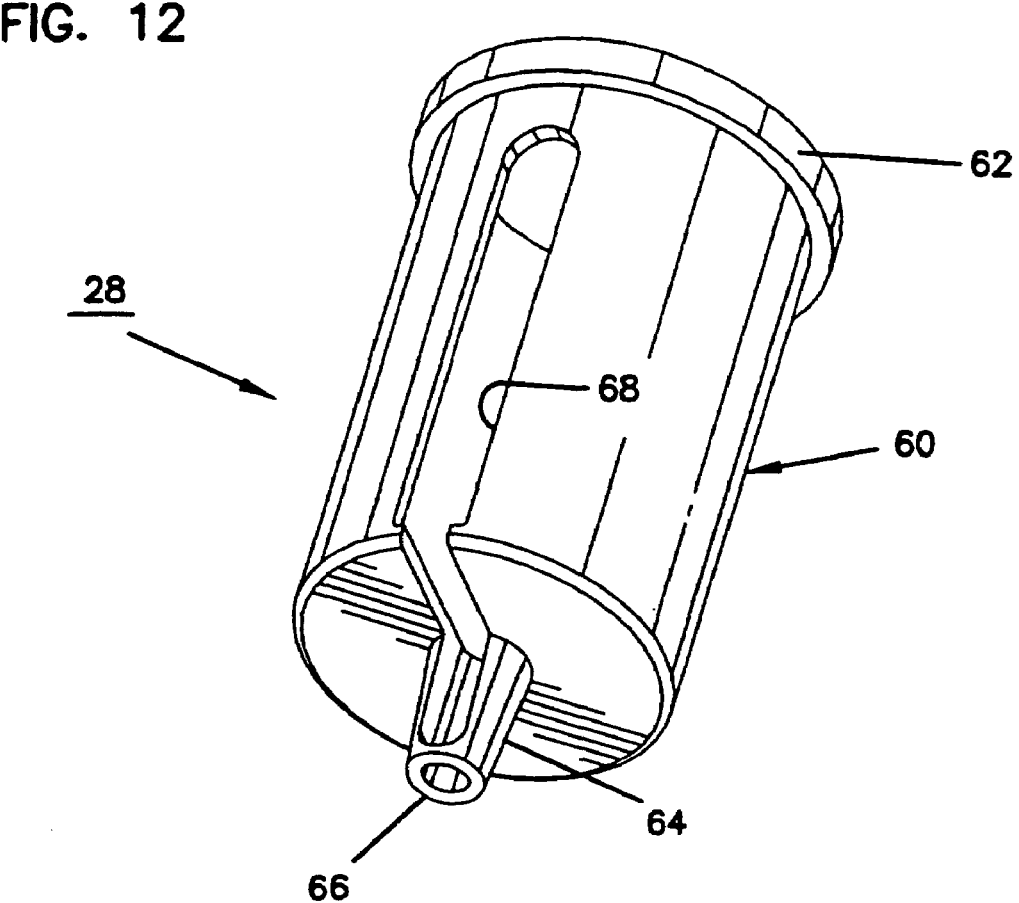
FIG. 12 is a perspective view of a shell for use in the apparatus of FIG. 1.
Figure 13:
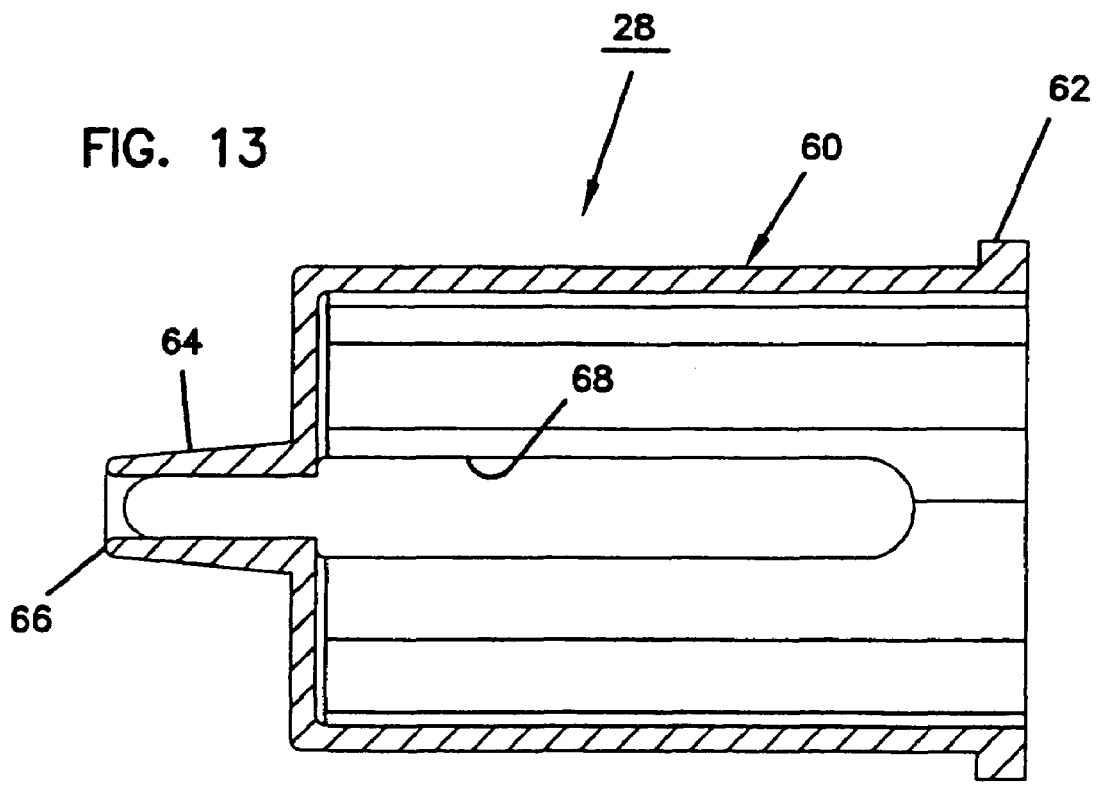
FIG. 13 is a sectional view of the shell of FIG. 12.

The shell 28 is separately shown in FIGS. 12 and 13. The shell 28 includes a cylindrical body 60 sized to be slideably received in close tolerance within the reduced diameter cylindrical portion 54 of collar 26. The cylindrical body 60 terminates at a flange 62 positioned to abut stop surface 56 of collar 26. Accordingly, the shell 28 is slideable within the collar 26 with the flange 62 movable between the stop surface 56 of collar 26 and the end plate 36 of base 24.

The cylindrical body 60 has at its end opposite flange 62 a reduced diameter portion 64 which is coaxial with the main cylindrical body 60. The reduced diameter portion 64 terminates at a first pressure ring 66 with the plane of the opening of the pressure ring 66 being generally perpendicular to the cylindrical axis of body 60. An elongated slot 68 extending generally in the direction of the axis of body 60 is provided extending through the shell 28 with the slot 68 extending substantially the length of the body 60 and substantially the length but not entirely through the sidewall of the reduced diameter portion 64 such that ring 66 is an uninterrupted ring. However, a segmented ring or other incomplete ring would be satisfactory.

The optics housing 30 is separately shown in FIGS. 7–11 and includes a generally cylindrical main body 70 (with flat side walls 71a, 71b) having extending axially therefrom a reduced diameter cylinder 72 (surrounded by surface 71) having an annular slot 73. The reduced diameter cylinder 72 is sized to be slideably received within the inner cylinder 40 of base 24 as best shown in FIGS. 1 and 2.

The main body 70 includes a first axial slot 74 extending partially through a distal end 75 of the body 70. Disposed axially spaced from slot 74 is a second slot 76 extending through the main body 70. A pin receiving hole 77 extends through body 70 perpendicular to slot 76. Ninety degrees offset from slots 74, 76 are access holes 78 in communication with a hollow interior 80 of cylinder 72. Ninety degrees offset from slot 74 are pockets 82, 83 with axes of the pockets 82, 83 in coaxial alignment with one another and in communication with the slot 74. The base end 75 has a ramped ridge 79 extending parallel to hole 77.

In the assembly, as best shown in FIGS. 1 and 2, a first biasing spring 84 is positioned to act between the base plate 36 of base 24 and the flange 62 of shell 28 urging the shell 28 away from the base plate 36. A second biasing spring 86 is positioned to act against the base plate 36 of base 24 and an engaging surface 71 on cylinder 70 thereby urging the optics housing 30 axially away from the base plate 36.

As shown in FIGS. 3–6, a light source 90 is contained within pocket 82. A light detector 92 is contained within pocket 83. Electrical leads (not shown) from both the light source 90 and light detector 92 may be passed between the opposing exterior surfaces 71a, 71b of cylinder 70 and the interior surface of shell cylinder 60 with the leads then passed through the holes 78, into hollow interior 80 of cylinder 72 and directed thus into the circuitry (not shown) contained within the housing 22. The light source 90 and light detector 92 are aligned to define a light path therebetween. The light source 90 generates a testing wavelength. The light detector 92 is selected to measure the intensity of wavelengths including the intensity of the testing wavelength.

Figure 26:
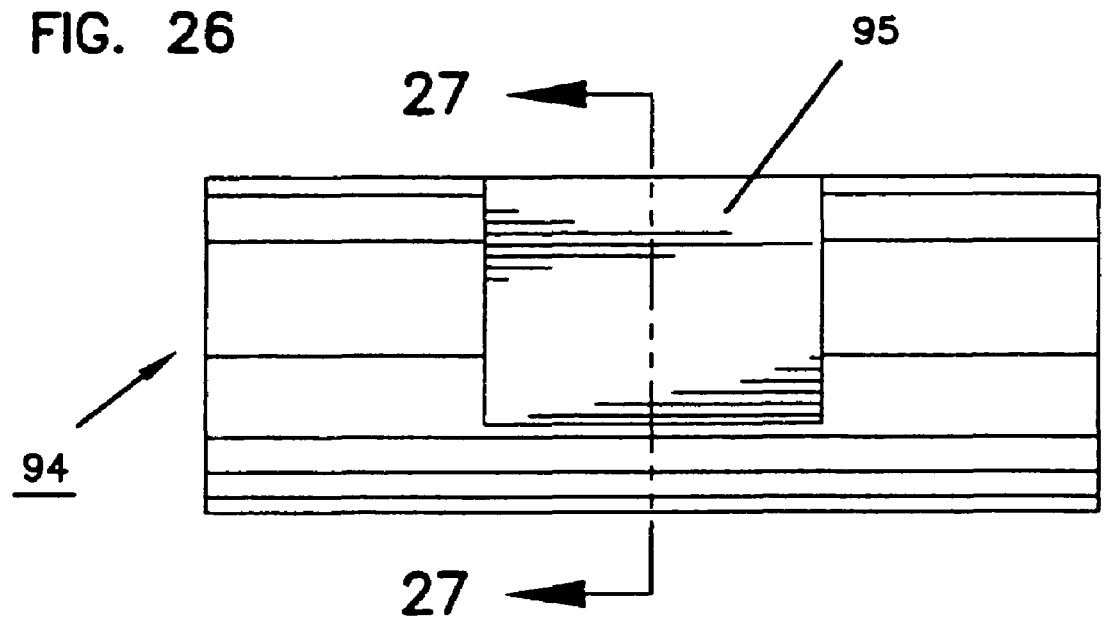
FIG. 26 is a side elevation view of a catch pin for the sampler of FIG. 18.
Figure 27:
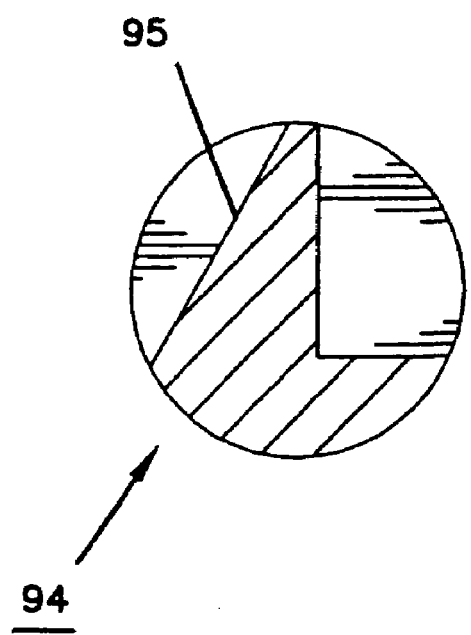
FIG. 27 is a view taken along line 27—27 in FIG. 26.
Figure 35:
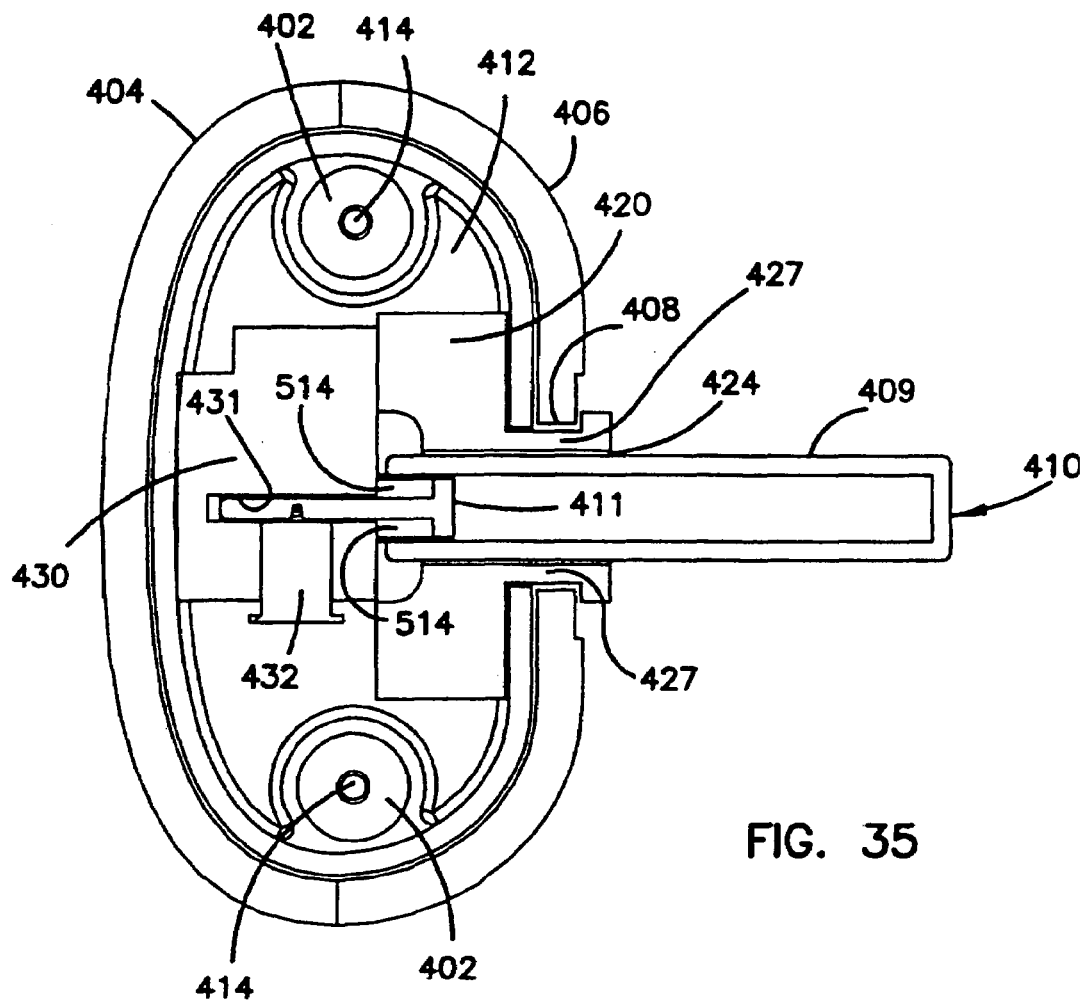
FIG. 35 is a transverse cross-sectional view of the embodiment of FIG. 32.
Figure 32:
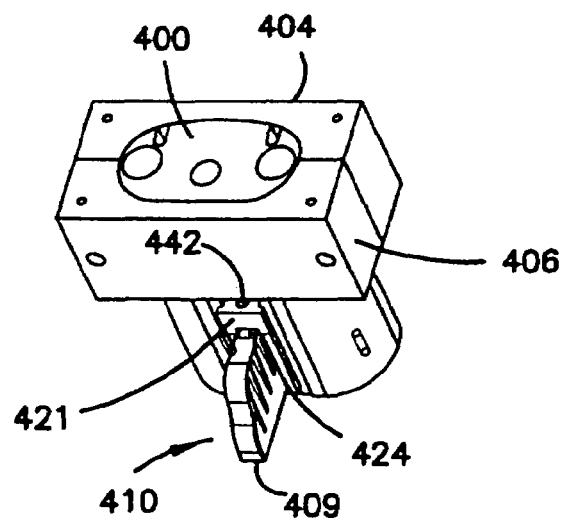
FIG. 32 is a top, front, right side perspective view of an alternative embodiment of the present invention.
Figure 33:
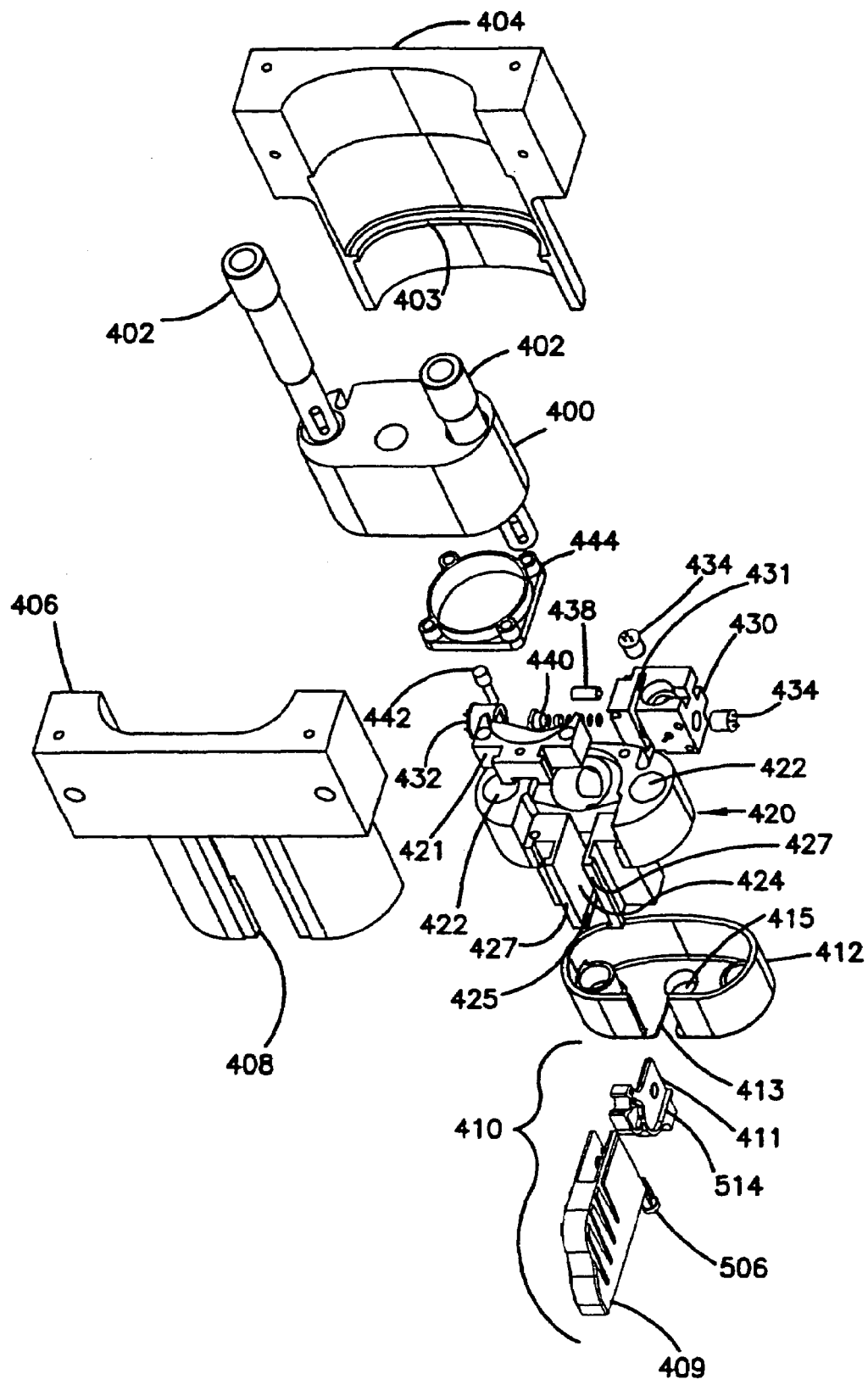
FIG. 33 is an exploded view of the alternative embodiment of FIG. 32.

A lock pin 94 (shown separately in FIGS. 26–27) is contained within optics housing 30 in hole 77 with the lock pin 94 positioned at a 90° angle to the plane of the slot 74. The pin 94 has a ramp 95 disposed in slot 76. In the assembly shown in FIGS. 1–6, the slots 74, 76 of the optics housing 30 are in alignment with the slot 68 of the shell 28.

As shown in FIGS. 18–25, the sampler 32 includes a body 100 formed of injection molded plastic. The body 100 includes a rear handle portion 101 and a forward sampling portion 102. The handle portion 101 is sized to be gripped by the fingers of a user. At the sampling end 102, the body 100 is provided with a hub or piston 104. The piston 104 is cylindrical and sized to be received in close sliding tolerance within the reduced diameter cylinder 64 of shell 28. The piston terminates at a flat second pressure surface 106 which is generally perpendicular to the axis of the needle 10. While a flat surface 106 is preferred, other shapes (e.g., concave) could be used.

The needle 10 protrudes beyond the surface 106 a distance equal to a desired penetration of the needle 10 into a patient's skin layer. As disclosed in the aforementioned international publication, distance of protrusion of needle 10 is about 1.5 mm to ensure protrusion of the needle 10 into but not through a dermal layer of a patient's skin. At the sampling end 102, the main body 100 is provided with a relief 108 surrounding a hole 110 formed through the body. The hole 110 is in communication with a proximal end 11 of the needle 10. Accordingly, an absorbent material 12 such as the material 210' shown in FIGS. 16–20 of the aforementioned International Publication No. WO95/10223 may be placed within the relief 108 such that interstitial fluid which flows up the needle 10 will be deposited upon the material 12. The material 12 is held in place through any suitable means such as by an adhesive ring 111 (or, alternatively, ultrasonic bonding or other bonding technique).

The hole 110 is positioned at a sampling location such that the hole 110 is in the light path between the light source 90 and the light detector 92 when the sampler 32 is placed within the apparatus 20 as will be described. The end 102 is sized to be received within the aligned slots 68, 74 of shell 28 and optics housing 30, respectively.

The main body 100 is provided with an arcuate rib 113 sized and shaped to abut an exterior surface of is the optics housing 30 on both sides of the slot 74 and to curve beneath the base 75. A latching member 112 is connected to the body 100. The latching member 112 pivots at a point of connection to the body 100 and includes a lever arm 114 exposed at the handle portion 101 such that the lever member 114 may be depressed manually by a user. The latch 112 further includes a latching end 116 sized and positioned to be received within the hole 76 of the optics housing 30. The latching end 116 includes a detent 118 (FIGS. 1–2) positioned to engage and receive the ramp 95 of the lock pin 94 within the detent 118 when the sampler 32 is inserted within the slots 74, 76 in a predetermined alignment and with the sampling location 110 disposed within the light path between the source 90 and detector 92. A leading end of the locking end 116 is provided with a ramped surface to ride over the pin 94 upon insertion of the sampler 32 within the optics housing 30 and to provide a positive lock as the pin is received within the detent 118. To further secure the sampler 32 in optics housing 30 in the desired alignment, sampler housing 100 has a detent 117 (FIG. 23) to receive ridge 79 on the base 75 of optics housing 30. The sampler 32 may be easily removed by a user depressing end 114 thereby raising end 116 for the pin 94 to clear the detent 118 permitting removal of the sampler 32 from the apparatus.

With the construction thus described, a sampling end 102 may be placed within the aligned slots 74, 68. over-insertion is avoided by reason of the sampling end 102 butting up against the interior of the optics housing 30. Further, the lock pin 94 received within the detent 118 and the ridge 79 in detent 117 ensure that the sampler 32 is not under-inserted into the slots 74, 76 by providing a user with a positive feedback indicating that the lock pin 94 has been received within the detent 118 indicating the sampler 32 is in the predetermined alignment. Accordingly, upon receipt of such feedback, the user is assured that the sampling location 110 is in alignment with the light path between the light source 90 and the light detector 92.

The first spring 84 urges the shell away from the base 24 such that the full length of the piston 104 and needle 10 may clear the first pressure ring 66 and be inserted through the slot 68 as the sampler 32 is loaded into apparatus 20.

Due to the locking at detents 118 and 117, sampler 32 is held in a predetermined alignment with the membrane 12 in the light path between light source 90 and light detector 92. To facilitate placement of sampler 32 within apparatus 20, the sampler 32 and apparatus 20 have mating external geometries. Namely, in the rest position of FIG. 1, the shell 28 is fully extended from base 36 by spring 86. Slot 58 of collar 26, slot 68 of shell 28 and slot 74 of optics housing 30 are aligned to permit insertion of end 102 of sampler 32. Further, in this position, slot 68 is sized so that needle 10 may pass ring 66 without interference. Also, in this position, slot 61 of collar 26, slot 68 of shell 28 and hole 76 of optics housing 30 are aligned to receive end 116 of lever arm 112.

Upon insertion, the mating geometry of sampler 32 and optics housing 30 insure the membrane 12 is accurately positioned. The ribs 113 acting against the external surface of optics housing 30 together with ribs 95, 79 received within detents 118, 117 securely couple the sampler 32 to optics housing 30 in accurate alignment and with the sampler 32 movable with the optics housing 30. As the optics housing 30 moves relative to shell 28 and collar 26, the sizing of slots 58, 61 and 68 avoid interference with movement of the sampler 32.

Upon initial placement of the apparatus against a patient's skin 200 (FIG. 28), the ring 66 first contacts a patient's skin 200 with the needle 10 being recessed behind the ring 66. Upon urging of the apparatus 20 against the skin 200, the ring 66 moves relative to the needle 10 against the bias of the first spring 84. Upon achieving such relative movement, the needle 10 then penetrates the skin 200 with the second pressure surface 106 of the piston 104 engaging the skin and with both springs 84, 86 resisting further penetration until both springs are compressed. Second spring 86 ensures a constant force acts on piston 106.

FIGS. 28–30 show a sequence of operation of the present apparatus. As shown in FIG. 28, during the rest state, the needle 10 is recessed behind the first pressure ring 66 to prevent damage to the needle 10 and inadvertent skin penetration. Upon initial urging of the pressure ring 66 against the skin (FIG. 29), the pressure ring 66 depresses the skin 200 and makes the skin taut in the area defined by the ring 66. Further, the pressurization creates a pressurized area in the zone of the skin layer 200 directly beneath the ring 66. This is desirable since interstitial fluid beneath the skin 200 is believed to exist at a negative pressure. Creating a pressurized zone beneath the ring 66 is believed to assist in rapid collection of interstitial fluid within the needle 10. During this initial pressurization of the skin 200, the ring 66 moves relative to piston 104 until the needle 10 penetrates the skin 200 and the end 106 of the piston 104 abuts the skin 200 (FIG. 30). Further depression (which can occur against soft skin but which may not occur against more rigid skin) is shown in FIG. 31 where the piston end surface 106 protrudes slightly beyond the ring 66 to further increase the pressure acting in the collection zone of the skin 200 and with full penetration of the needle 10.

It has been found that this sequence of action significantly increases the rate at which interstitial fluid is collected through the needle 10 and deposited on the membrane 12 within the sampler 32.

After full penetration of the needle 10, internal circuitry may then be actuated to operate the light source 92. Absorption of the testing light through the collected sample provides an indication of the amount of the constituent contained on the sample.

In a preferred embodiment, springs 84, 86 are preloaded. Namely, in the rest position of FIGS. 1 and 28, first spring 84 exerts an urging force on shell 28 of about three pounds and with a spring constant of about four pounds per inch. Spring 86 is pre-loaded to about one pound and has a spring constant of about two pounds per inch. To accommodate the pre-loading of springs 84, 86, optics housing 30 is provided with a retaining ring 202 (shown only in FIGS. 1 and 2) in slot 73. The pre-loading of spring 84 insures a minimum skin pressure by ring 66 before penetration of the skin 200 by needle 10.

Figure 18:
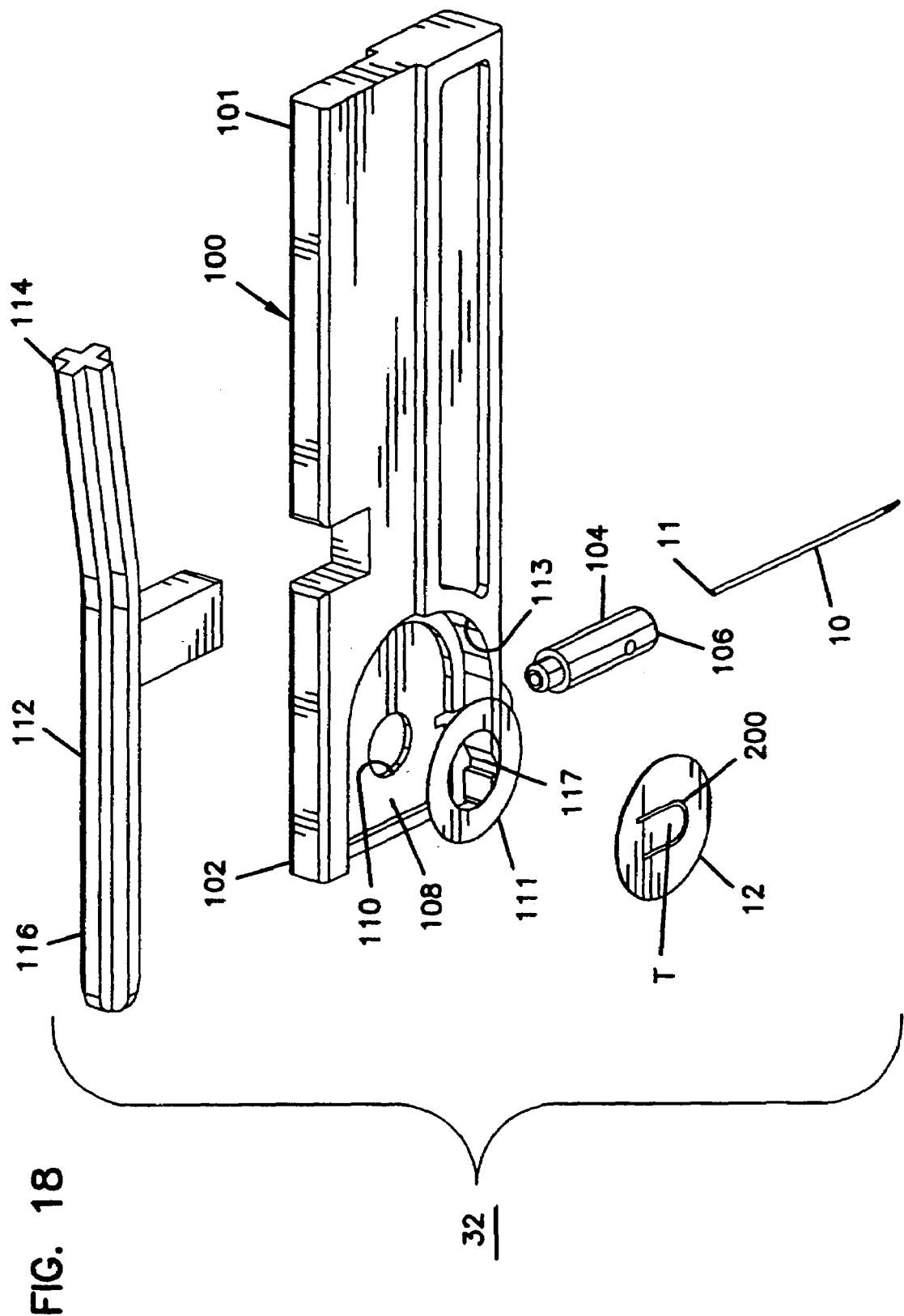
FIG. 18 is a top, left side and rear end exploded perspective view of a sampler for use in the apparatus of FIG. 1.
Figure 19:
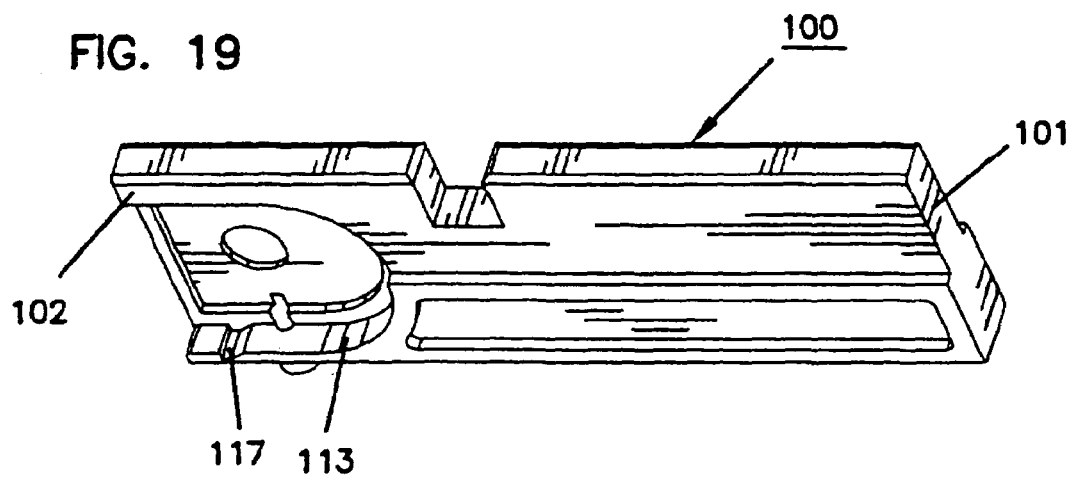
FIG. 19 is a top, left side and rear end perspective view of a sampler main body for the sampler of FIG. 18.
Figure 20:
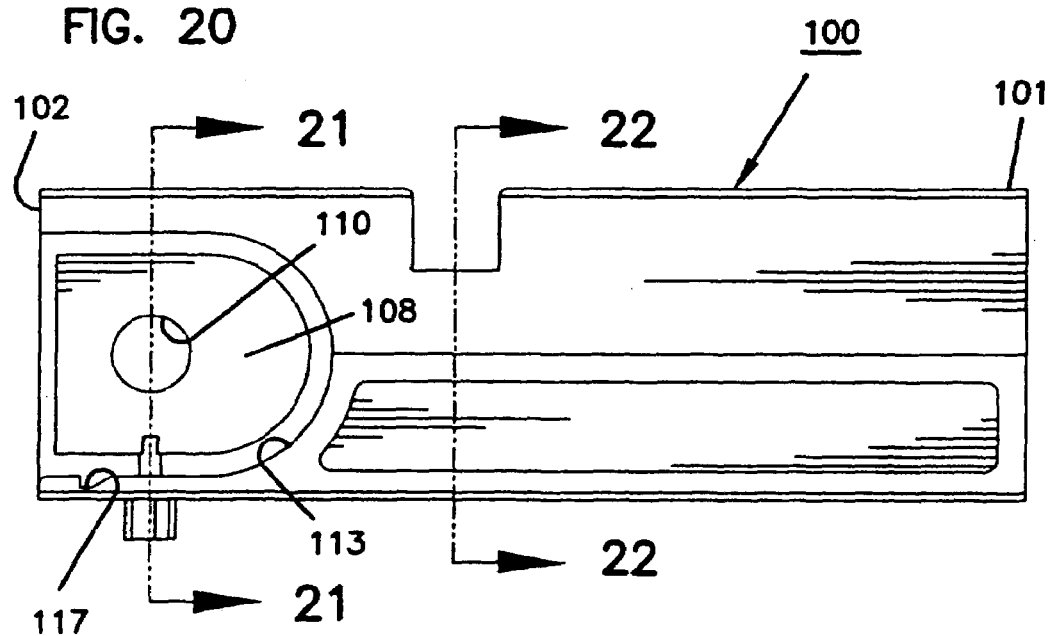
FIG. 20 is a left side elevation view of the sampler main body of FIG. 18 (with the opposite side being substantially identical)
Figure 21:
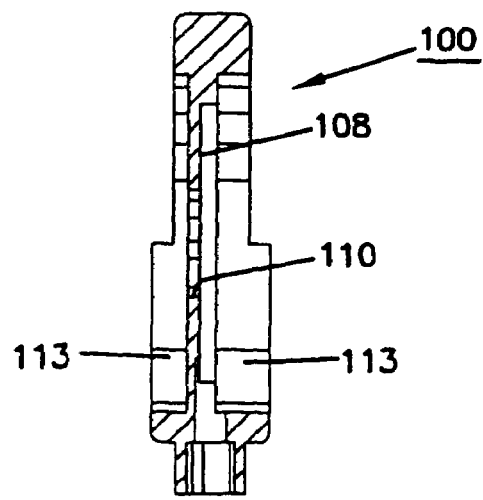
FIG. 21 is a view taken along line 21—21 of FIG. 20.
Figure 22:
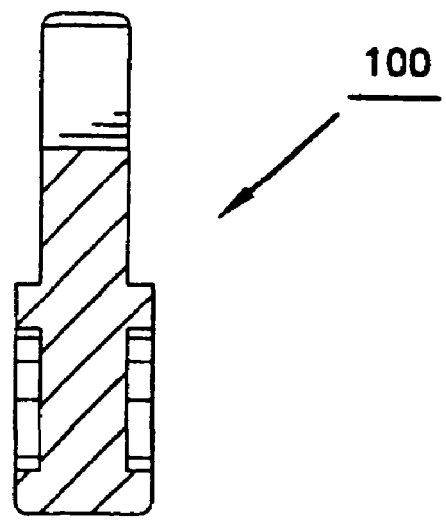
FIG. 22 is a view taken along line 22—22 of FIG. 20.
Figure 23:
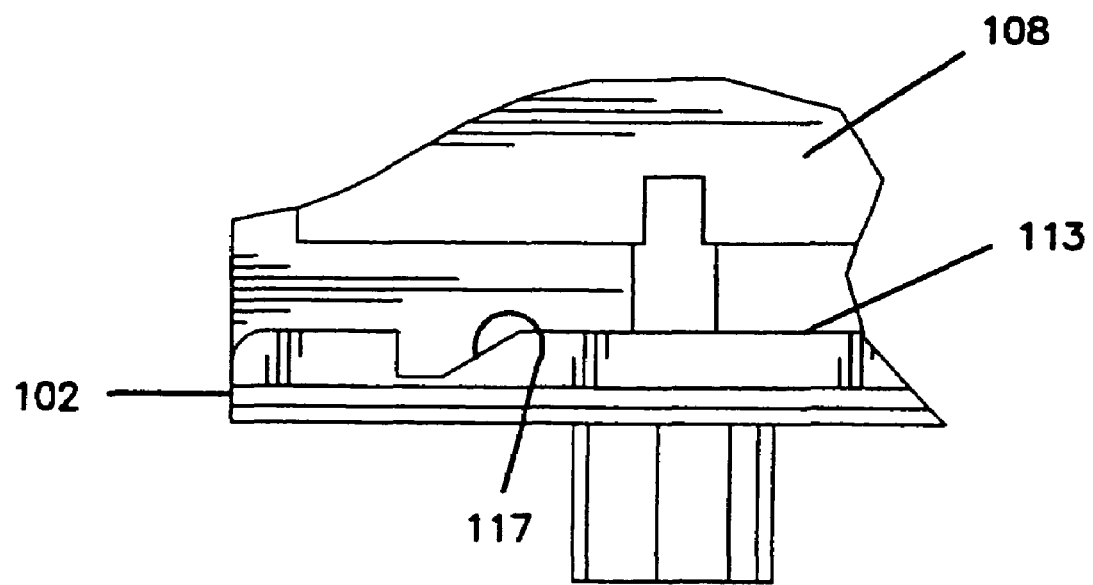
FIG. 23 is an enlarged bottom view of a front portion of the main body of FIG. 20.
Figure 24:
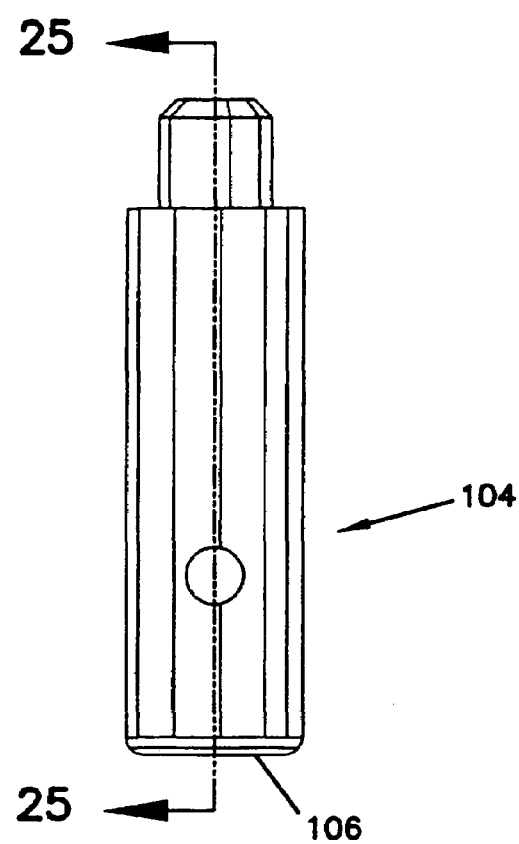
FIG. 24 is a side elevation view of a piston for the sampler of FIG. 18.
Figure 25:
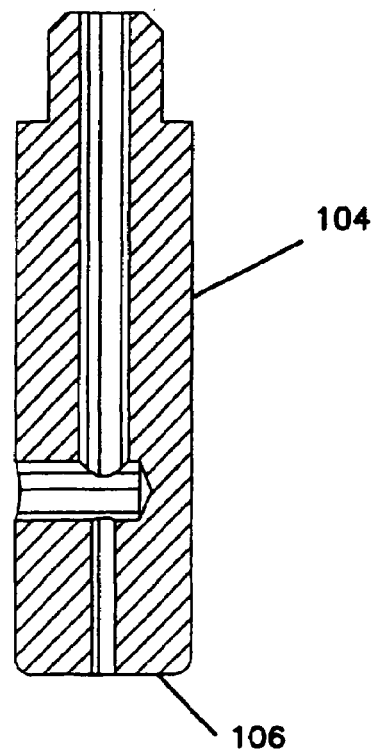
FIG. 25 is a view taken along line 25—25 in FIG. 24.

As shown best in FIGS. 1, 2 and 18, membrane 12 is provided with a U-shaped boundary 300. Boundary 300 is formed by ultrasonically or pressure treating membrane 12 to create a material density in boundary 300 which is greater than a material density of the remainder of the membrane 12. Therefore, boundary 300 provides an increased resistance to liquid flow compared to the remainder of the absorbent membrane 12. The end 11 of needle 10 is positioned to deposit interstitial fluid onto the interior of the U-shaped boundary 300. The increased density of the boundary 300 permits the fluid to flow within the interior of the boundary 300 but restricts fluid flow beyond the boundary 300. The target location ("T") of light through membrane 12 during testing is positioned within the boundary 300. Boundary 300 thus insures that a sufficient volume of collected fluid is in residence at the target location T during testing.

It will be appreciated that through use of the present invention the rate at which interstitial fluid is collected through the needle 10 is greatly enhanced over that shown in the aforementioned International Publication No. WO95/10223. Further, the sampling apparatus is contained within the low-cost sampler 32 which can be readily disposed of after each use. The mating geometry of the sampler 32 with the internal geometry of the apparatus 20 ensures that the sampler 32 is placed within the apparatus 20 in a predetermined alignment with the sampling location in the light path between the source 90 and the detector 92. The sampling apparatus also ensures a proper positive locking position which may be released easily by an operator and the entire operation of insertion of the sampler within the apparatus and removal of the sampler for subsequent disposal is easily accomplished for a patient.

B. Second Described Embodiment

FIGS. 32 through 39 illustrate an alternative embodiment of the present invention. In these figures, the base 24 of the previous described embodiment as well as collar 26, shell 28 and optics housing 30 are replaced with a piston housing 400 which slideably receives two hollow pistons 402. The pistons 402 are disposed to move in generally parallel paths of travel relative to the piston housing 400.

Figure 34:
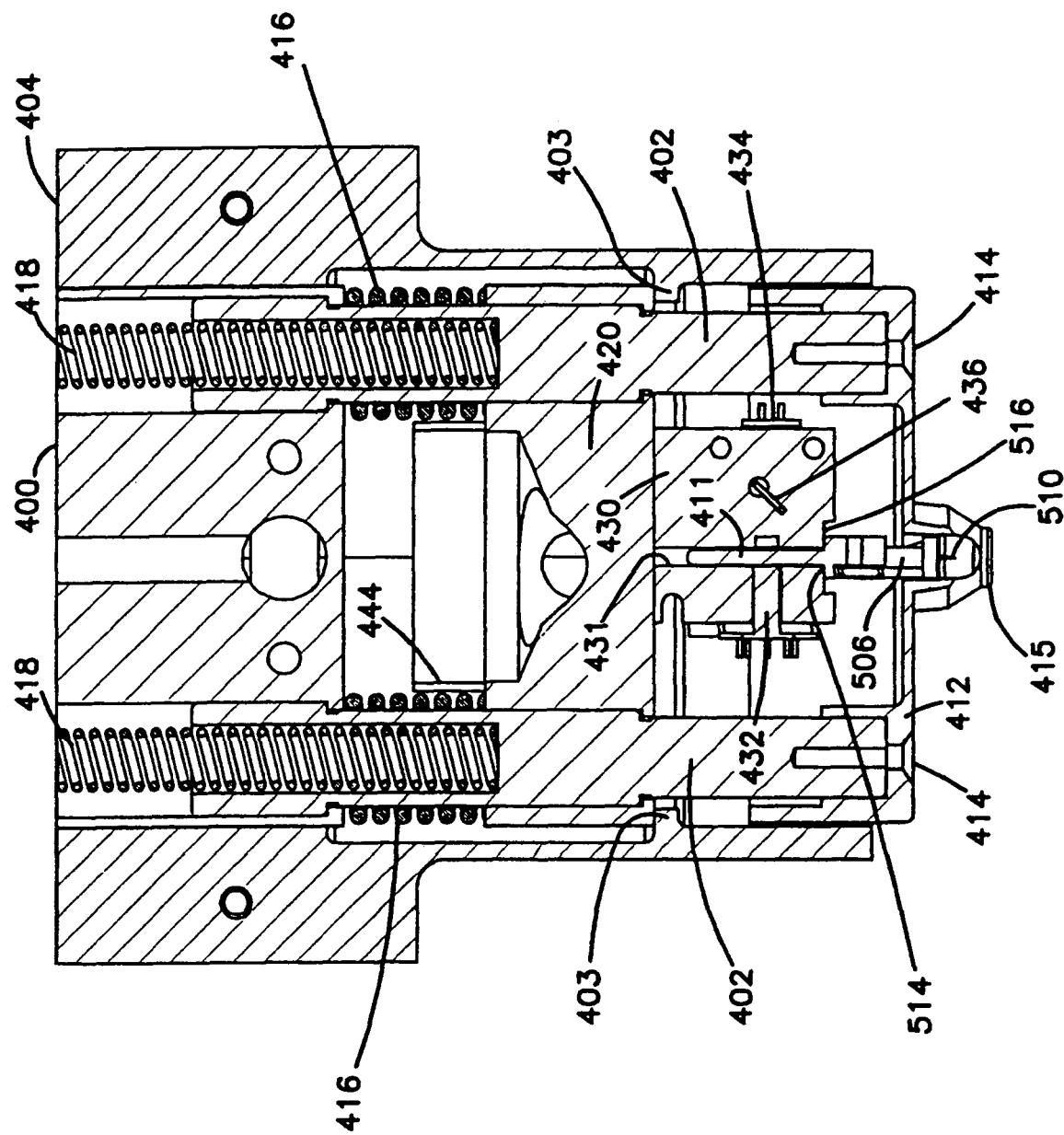
FIG. 34 is a cross-sectional view of the embodiment of FIG. 32.

The piston housing 400 is retained in a stationary position (relative to tool handle 22 of FIG. 1) by means of clam shell back 404 which is adjoined to claim shell front 406. The clam shells 404, 406 may be connected to the apparatus housing 22 as in the previous described embodiment. The clam shell front 406 has an axially extending slot 408. Bottom ends of the hollow pistons 402 are secured to a pressure ring shell 412 by means of screws or bolts 414 (FIG. 34). An optical core 420 is provided with the pistons 402 passing through aligned holes 422 of the core such that the core 420 is movable relative to the piston housing 400 and the pistons 402. A flange 403 on clam shells 404, 406 limits downward movement (in the view of FIG. 34) of optical core 420.

Best shown in FIG. 34, outer springs 416 surrounds the pistons 402 between the piston housing 400 and the optical core 420 such that springs 416 compress when the movable optical core 420 moves upwardly (in the view of FIG. 34) relative to the stationary piston housing 400. Further, springs 418 are positioned within each of the hollow pistons and opposing the housing 22 (not shown in FIG. 34 but shown in FIG. 1) such that the springs 418 are compressed as the pressure ring shell 412 and the pistons 402 move upwardly (in the view of FIG. 34). The optical core 420 included a block member 421 as a separate element to permit ease of machining of optical core 420. The optical core 420 has an axially extending slot 424 (defined by walls 427) on a forward side thereof (aligned with slot 408 on front clam shell 406) and sized to receive the sampler 410 as will be described. Further, the pressure ring shell 412 has an axial slot 413 (aligned with slot 408). The walls 427 are received within slots 408 and 413.

An optics housing 430 is secured to the optical core 420 for movement therewith. The optics housing 430 carries an optical source 432 as well as optical detectors 434 and a beam splitter 436 (shown only in FIG. 34). The optical source 432 directs infrared light to the beam splitter 436 which splits the beams into signals, each directed to detectors 434, to enhance optical analyzing of the signal. The source 432 directs the infrared light through an optical path which passes through a slot 431 formed in the optics housing 430. Slot 431 is aligned with slots 424 and 408. A ball plunger 438 is urged by a spring 440 into slot 436. A cam pin 442 is carried in the deployment block 421 in order to protrude into the slot 424. Finally, a fan is preferably provided for drying any sample within the apparatus. While the fan impeller is not shown, the fan shroud 444 is shown into which a fan impeller may be placed for blowing air through the optical core 420 and the optics housing 430.

An enhanced design sampler 410 includes a handle end 409 and a sample end 411. The handle end 409 is a hollow sampler housing. The interior 500 of end 409 is sized to completely receive the sample end 411. The housing 409 is sized to be received within the slot 424.

Figure 36:
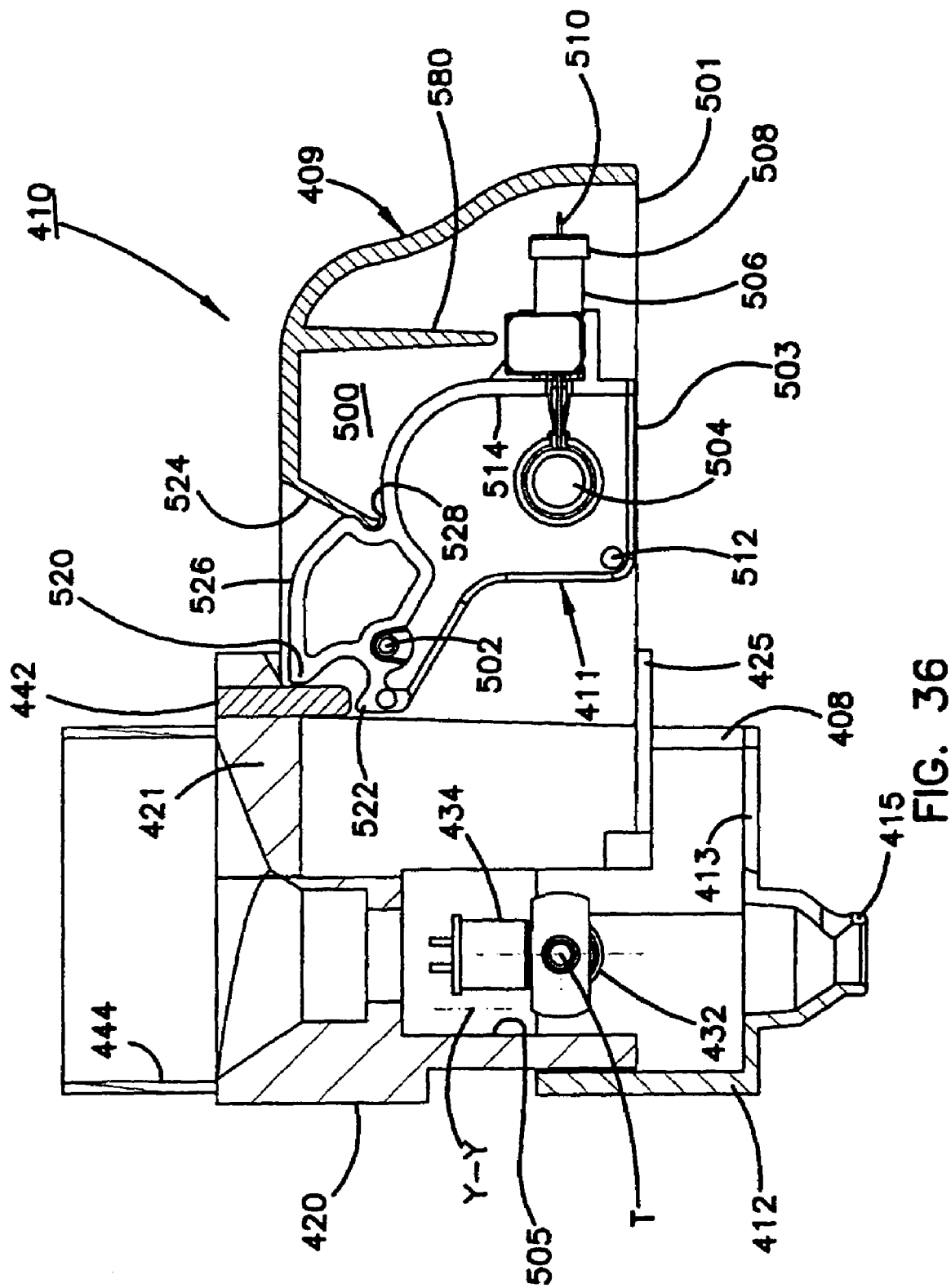
FIG. 36 is a partial sectional view of the embodiment of FIG. 32 showing initial insertion of a sampler into the apparatus.

As best shown in FIG. 36, side walls of the housing 409 have bottom edges 501 which are positioned against and ride on inwardly protruding rails 425 of the optical core 420 at the bottom of slot 424. The sample end 411 is pivotly secured to the sampler housing 409 at a pivot pin 502. As a result, the sample end 411 can pivot between a storage position shown in FIG. 36 with the sampler end 411 fully received within the interior 500 of handle 409 in order to protect the sample end 411 and its constituent components from destructive impact or contamination.

Figure 39:
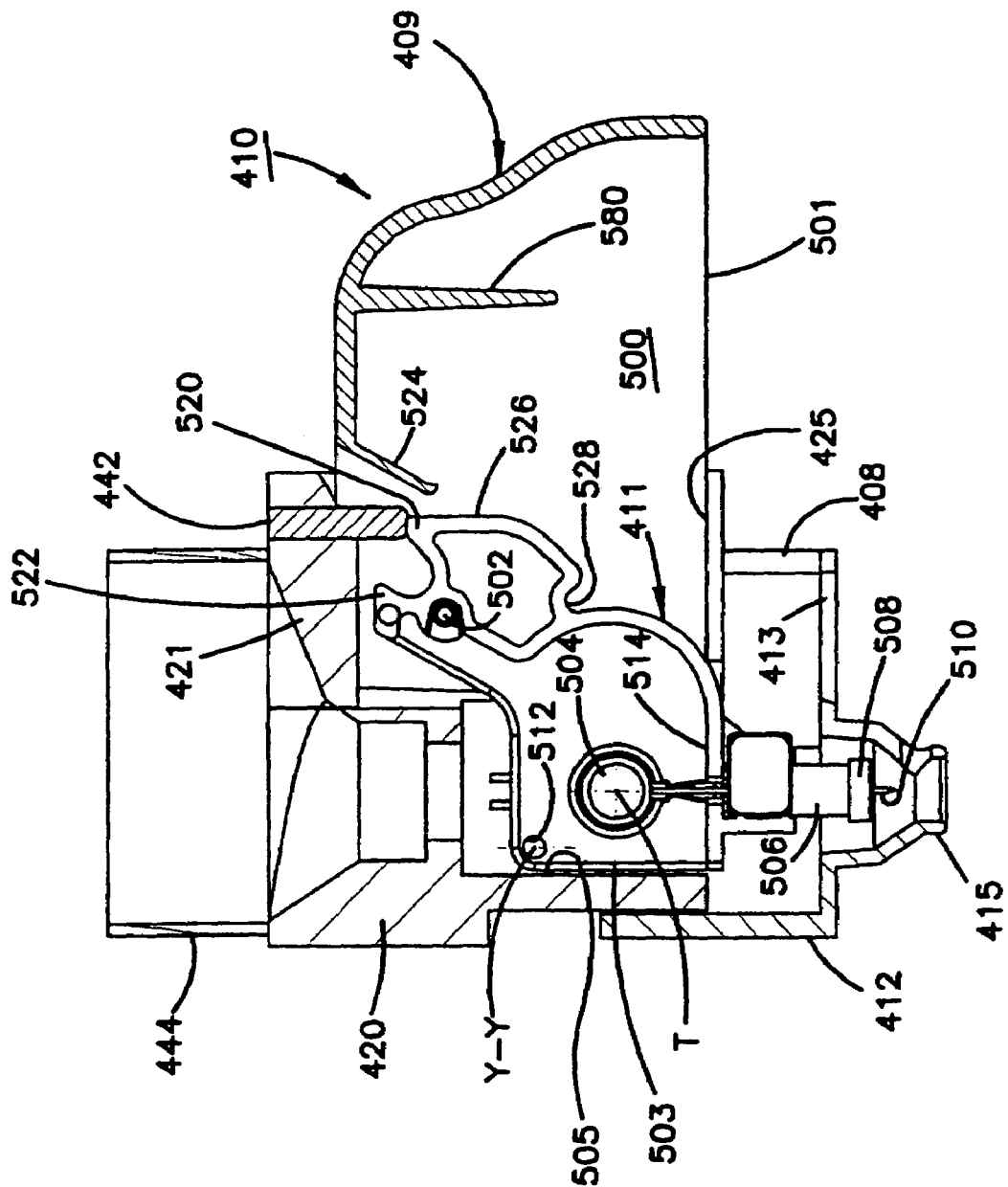
FIG. 39 is the view of FIG. 38 with the sampler fully inserted.

The sample end 411 can pivot from the storage position of FIG. 36 to a sample position shown in FIG. 39. The sample end 411 contains the membrane 504 for receiving a sample of interstitial fluid. Further, the sample end 411 contains a hub 506 terminating at a pressure ring 508. The hub 506 contains a needle 510 for collecting interstitial fluid and depositing the interstitial fluid on the membrane 501 as previously described.

In the storage position of FIG. 36, the membrane 504 is contained with the housing 409 to prevent damage as well as contamination (such as from finger prints or other skin oil). Further, in the storage position, the needle 510 is protected from damage as well as protecting a user from undesired contact with the needle 510.

In the sample position of FIG. 39 with the sampler 410 fully inserted, the membrane 504 is positioned in the optical pathway, T, between the light source and the light detectors. Further, the needle 510 is positioned centrally aligned with the pressure ring 415. The hub 506 and ring 508 are sized to freely pass through the ring 415. Also, in the position of FIG. 39, the ball plunger 438 (shown only in FIG. 33) moves along an axis Y—Y to be received within in a detent 512 formed within the sample end 411 in order to retain the sample end 411 in position.

When in the sample position, flanges 514 on the sample end 411 oppose and abut against a stop surface 516 on the optics housing 430, (FIG. 34). As a result, the opposition of the flanges 514 and surface 516 prevents upward movement of the sampler relative to the optics housing 430. Simultaneously, opposition of the bottom edges 501 to the rails 425 prevents downward movement of the sampler 410 relative to the optics housing 430. The reception of the ball plunger 438 within the detent 512 restricts left and right movement (within the view of FIG. 39) of the sampler 410 relative to the apparatus. Further, such reception of the ball plunger 438 within the detent 512 provides a tactile sensation to the user indicating that the sampler 410 has been fully seated with the apparatus. With the sampler 410 fully received with the apparatus, the membrane 504 is positioned within the light path, T, and the needle 510 is axially aligned with the hub.

Figure 37:
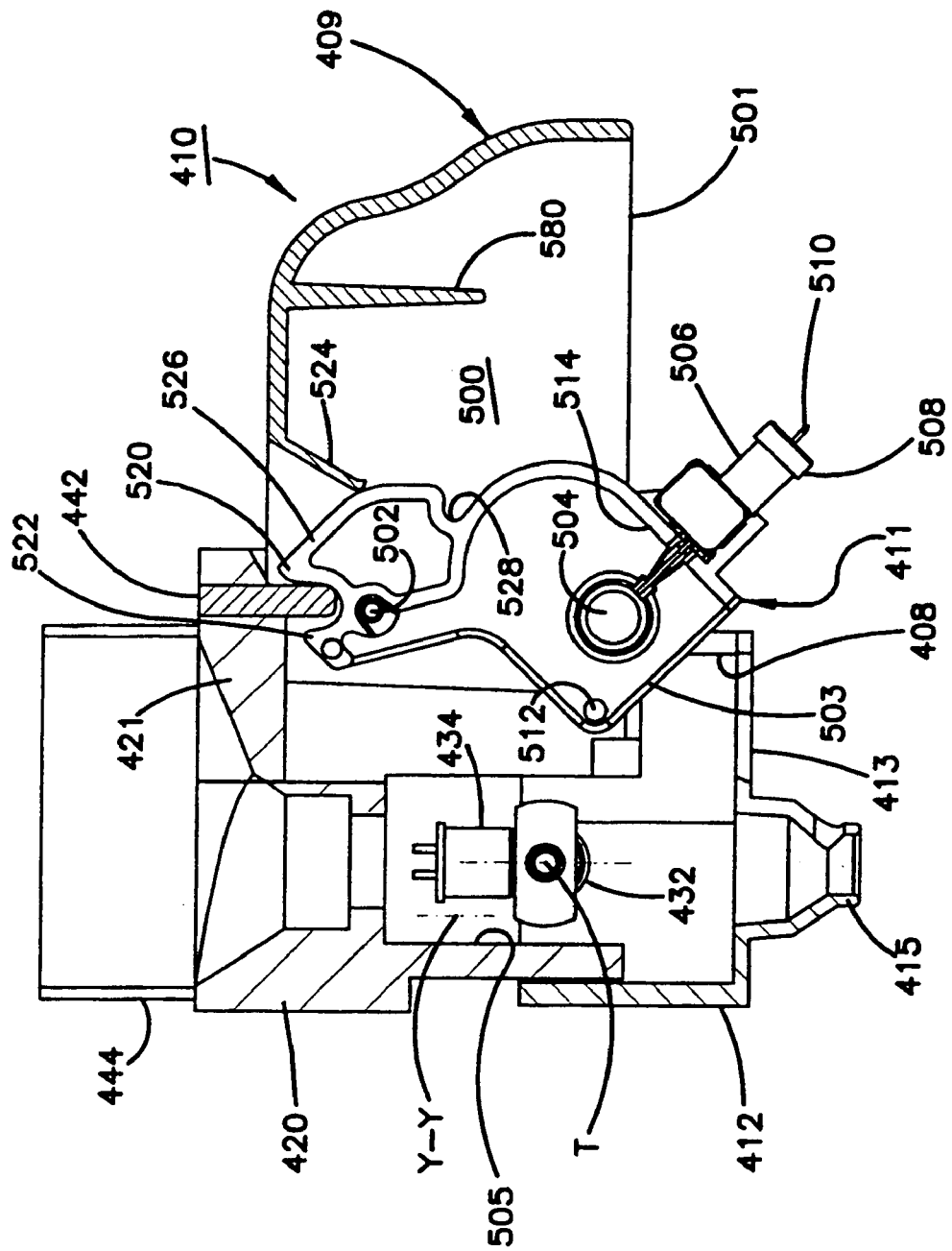
FIG. 37 is the view of FIG. 36 showing further insertion of the sampler into the apparatus for a cam to engage a cam follower.
Figure 38:
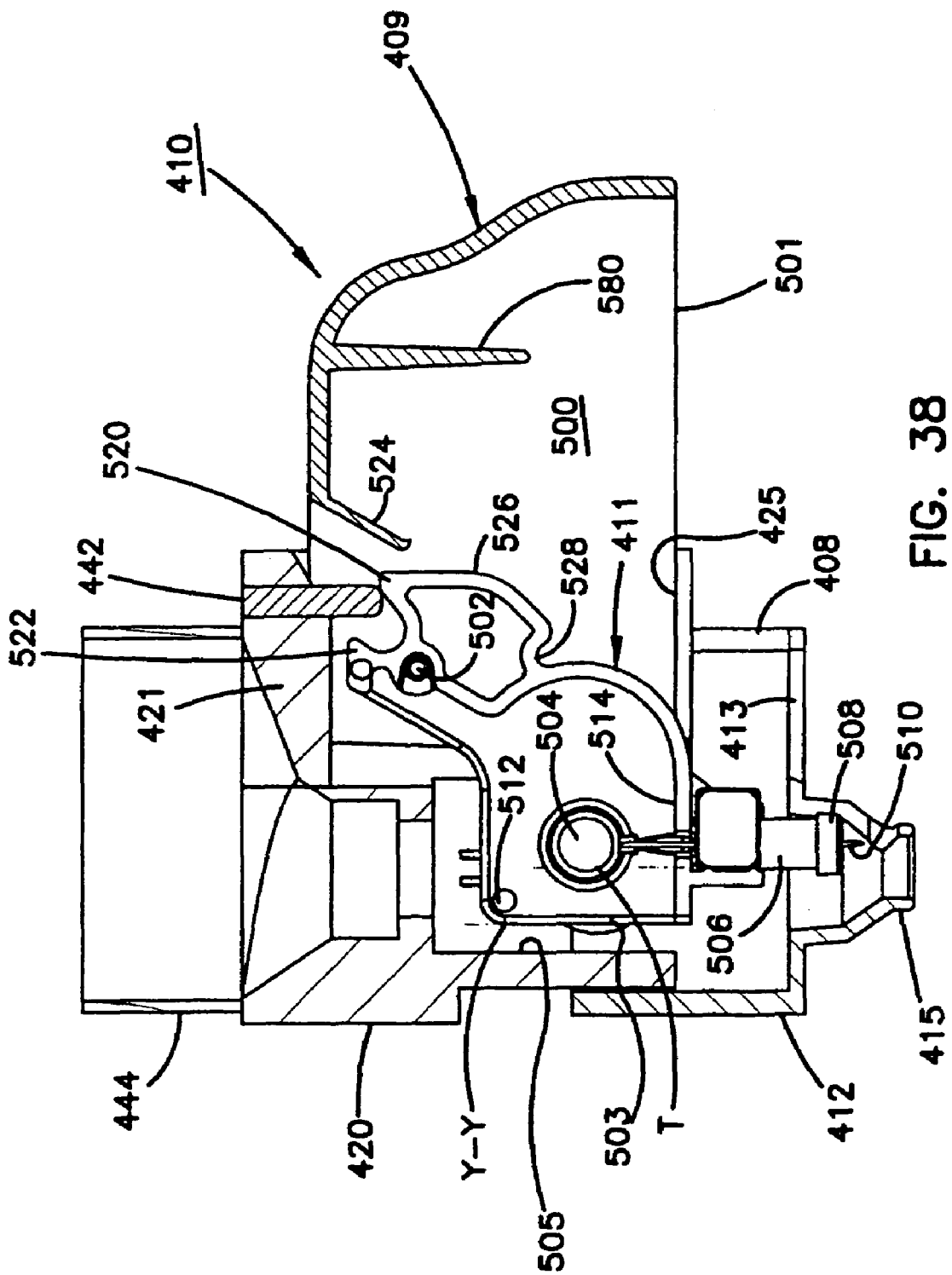
FIG. 38 is the view of FIG. 37 showing still further insertion of the sampler with a sample end pivoted to a sample position and with the sampler not yet fully inserted.

The sample end 411 is pivoted to the sample position of FIG. 39 as the housing 409 is urged within the slot 424. Specifically, the cam 442 abuts a first cam follower 520 on the sample end 411. FIGS. 36 through 39 illustrate the sequence of operation for pivoting the end 411 to the sample position. In FIG. 36, the sample end 411 is in the storage position and the handle 409 is in the process of initial insertion into the slot 424 with the bottom edges 501 of housing 409 riding on rails 425. The cam pin 442 is opposing the first cam follower 520. Upon further insertion of the housing such that the leading end 503 of the sample end 411 moves toward abutment with a wall 505 of the optical core 420 (FIG. 36), the cam pin 442 pushes against the cam follower 520 causing pivoting movement of the sample end 411 about the pivot pin 502 as illustrated in FIG. 37. FIG. 38 illustrates full pivotal movement of end 411 with end 411 not yet fully advanced to a full seated position. FIG. 39 illustrates full insertion of sampler 410 with the detent 512 aligned with the axis Y—Y of the pin 438 and with the membrane 504 aligned with the optical pathway, T. The compression of cam pin 442 against surface 520 prevents downward pivoting of end 411 and edge 514 against stop surface 516 (FIG. 34) prevents upward pivoting thereby locking end 411 in place with pin 438 in detent 512 and with the target area of membrane 504 in the light path. At this point, the apparatus can be used by urging the ring end 415 against the skin (preferably in the arm region). In response to such urging, the pressure ring shell 412 and attached hollow pistons 402 move upwardly to compress the springs 418. Following initial upward movement of the ring 415 relative to the hub 506, the needle penetrates the skin and the hub end 508 further engages and pushes against the skin with causation of movement of the optical core 420 and attached optics housing 430 and sampler 410 against the urging of the springs 416. The thus described dual operation of two pressure rings 415, 508 operating against the urging of two springs 416, 418 is more fully described with reference to FIGS. 28 trough 31.

Figure 40:
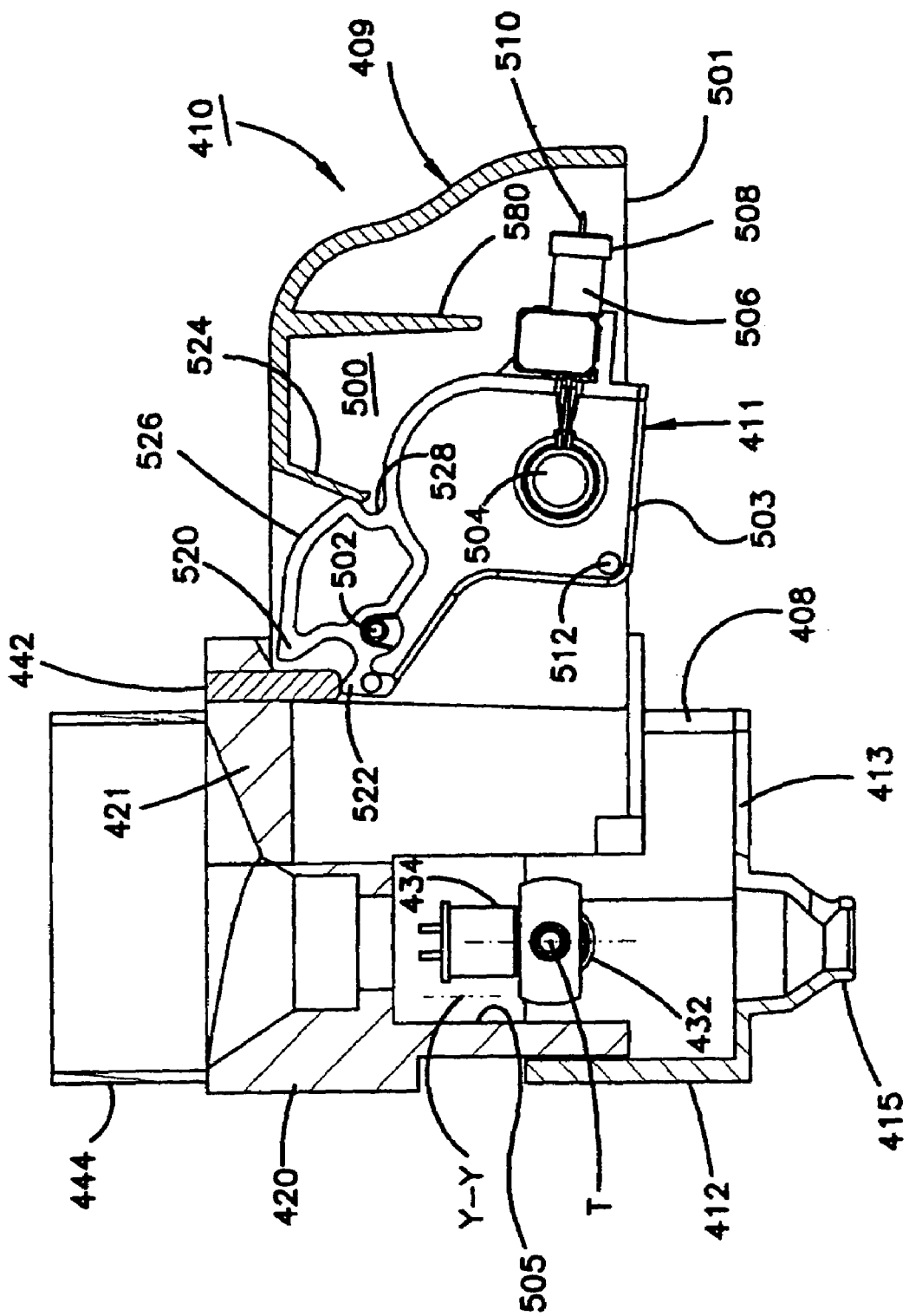
FIG. 40 is the view of FIG. 39 with the sampler partially withdrawn and with the sample end partially pivoted to a storage position by reason of the cam acting against a second cam follower.
Figure 41:
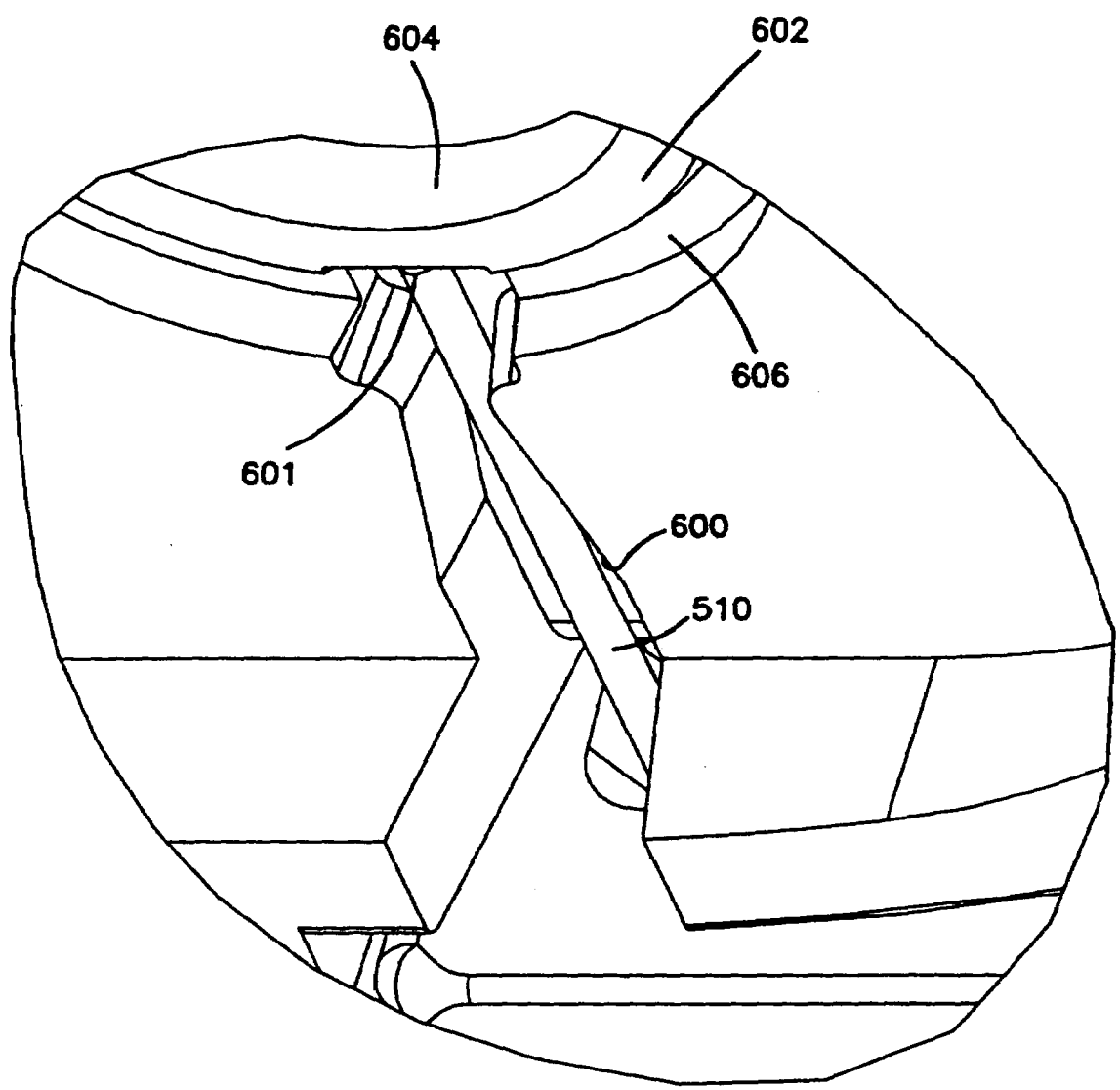
FIG. 41 is an enlarged view of relative positioning of a needle on a sampler with a membrane not shown.

After a fluid sample has been collected and/or tested, the patient can remove the tool from the arm such that the components return to the relative positioning shown in FIG. 34. At this point, the user can grasp the handle 409 to pull the sampler 410 out of the apparatus. This pulling causes the detent 512 to become disengaged from the ball plunger 438 and further causes the cam pin 442 to engage a second cam follower 522 as illustrated in FIG. 40. The engagement of the cam pin 442 with the second cam follower 522 urges the sampler end 411 to pivot from the sample position toward the storage position. An internal wall 580 acts as a stop to limit movement of end 411 and hold it in the full storage position.

The interior 500 of the housing contains a retention spring 524 on the housing 409. The retention spring 524 acts against an arcuate surface 526 on the sample end 411. The surface 526 terminates at a detent 528 to receive the retention spring 524. Therefore, when the sample end 411 is in the storage position of FIG. 36, the retention spring 524 is received within the detent 528 preventing movement of the sample end 411 out of the storage position until an adequate force acts on the cam follower 520 to cause pivoting movement around pivot pin 502.

When the sample end 411 is in the sample position of FIG. 38, the spring 524 has no deflection and is at rest. However, as the sample end 411 is moved from the sample position toward the storage position, the arcuate surface 526 engages the spring 524, causing the spring 524 to deflect and create a spring force. When the pin 442 acts against the second cam surface 522 (FIG. 40) to partially move the sample end 411 to the storage position, the deflected spring 524 is received within the detent 528 to thereby urge the sample end 411 to the full storage position and retain the sample end 411 in the full storage position.

Having described this second improved embodiment, it will be noted that the needle 510 and the membrane 504 are fully protected when the sampler 410 is not inserted into the apparatus. The membrane 504 and the needle 510 are only deployed after the housing 409 is initially inserted into the apparatus (i.e., into slot 424) with the cam pin 442 engaging the first cam follower 520.

C. Additional Enhanced Embodiments

In the embodiment of FIG. 1 and as disclosed in the aforementioned patent application Ser. No. 08/321,305 and 08/136,304 corresponding to PCT International Publication No. WO95-10223, the sampling needle such as needle 10 terminates at a free end 11 which has the plane of its opening perpendicular to the plane of the membrane 12. Stated another way, the longitudinal axis of the needle 10 is parallel to and spaced from the surface of the membrane 12.

Figure 42:
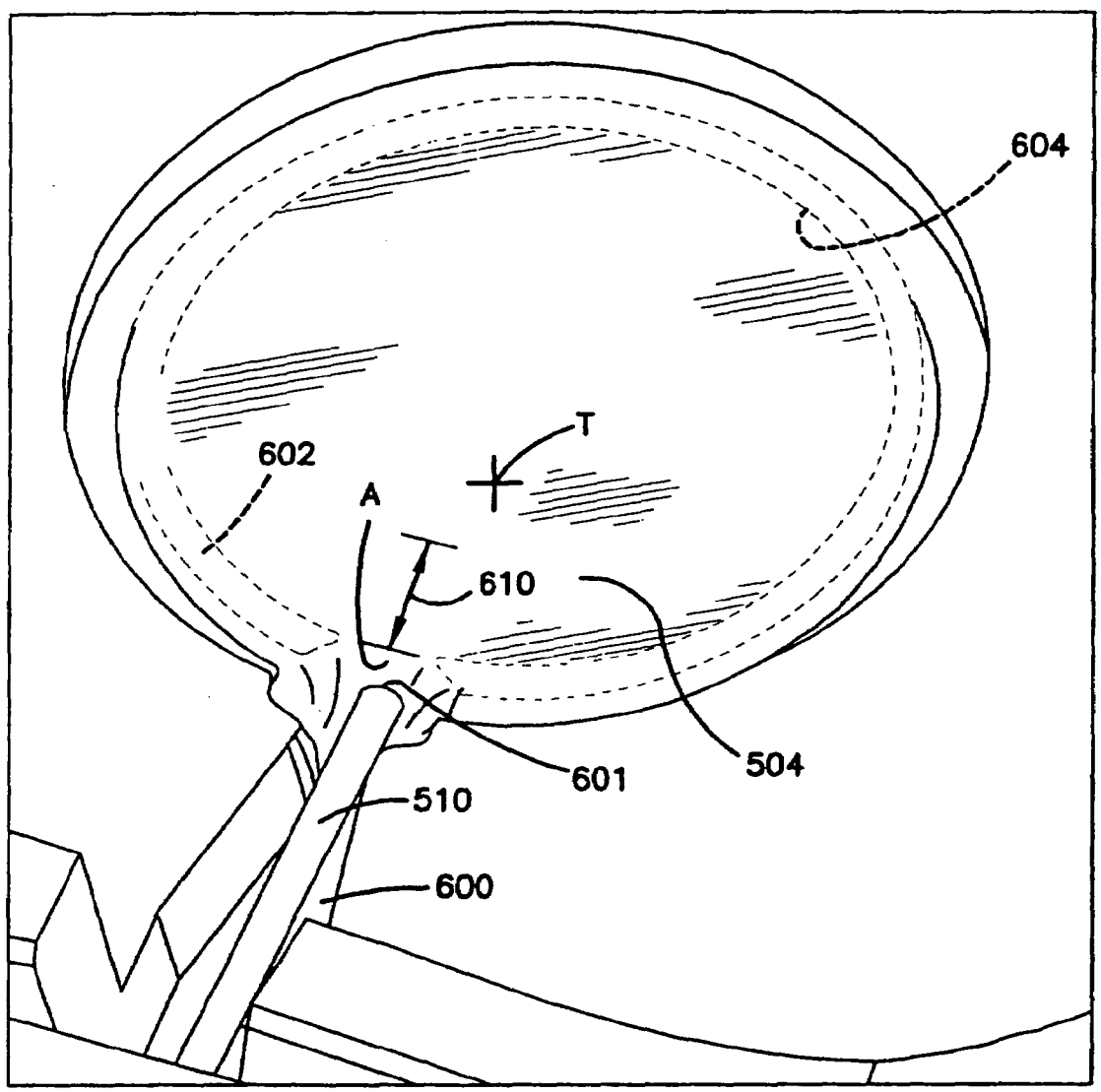
FIG. 42 is a perspective view of a needle and membrane assembly.
Figure 43:
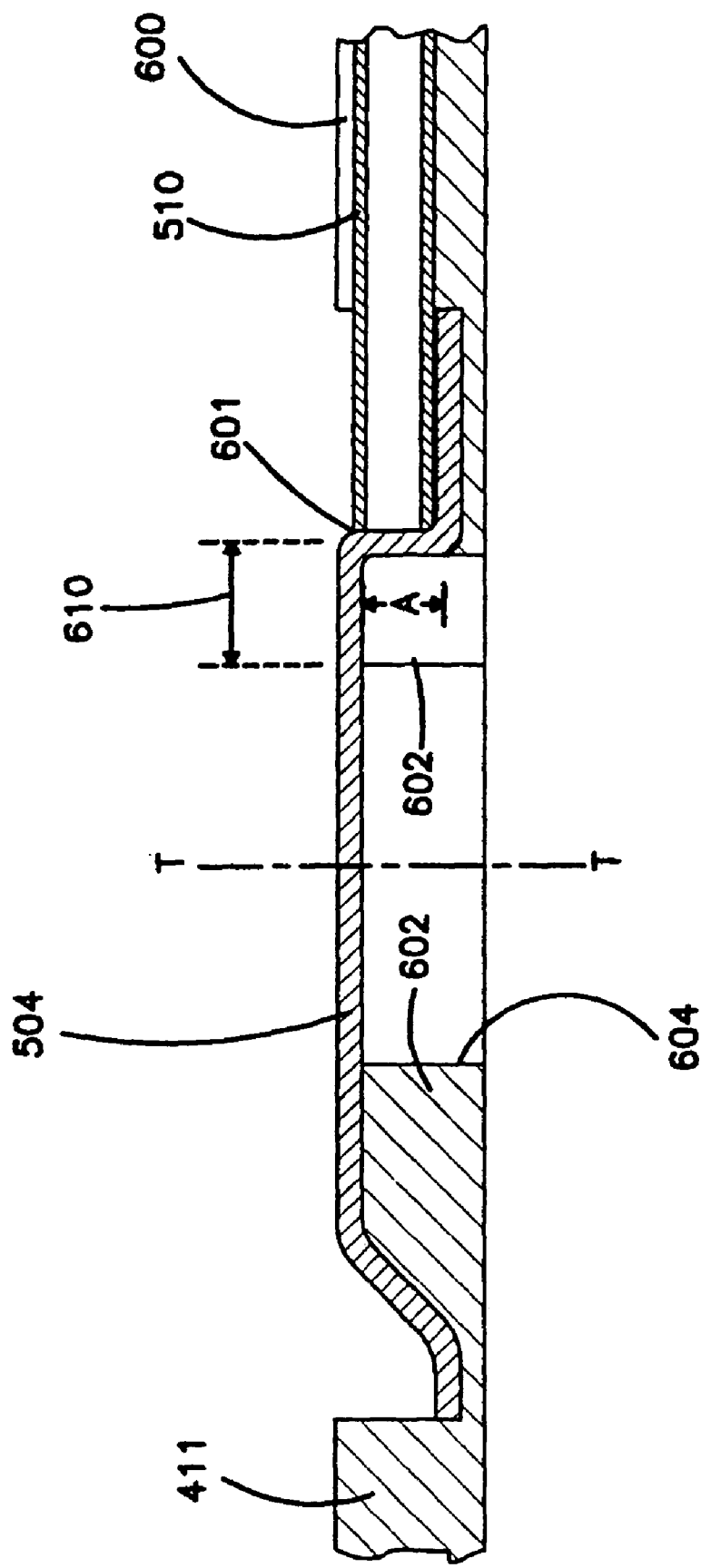
FIG. 43 is a cross-sectional view of FIG. 42.

The present embodiment of FIGS. 33–40 use an enhanced positioning of the needle 510 relative to the membrane 504. With attention to FIGS. 42 and 43, the sample end 411 includes a recess 600 sized to receive the needle 510. Further, the sample end includes a raised circular ring 602 surrounding the opening 604 through which the IR light is to pass. Between the ring 602 and the body of the sample end 411 an annular recess 606 is provided. The free end 601 of the needle 510 passes through the recess 600 and nearly abuts the ring 602. Accordingly, the membrane 504 can be placed on the ring 602 and depressed into the recess 606. The membrane 504 can then be secured within the recess 606 through any suitable means such as ultrasonic welding or the like. With this embodiment, the open end 601 is now disposed parallel to opposing material of the membrane 504 in a transfer area, A, of the membrane rather than perpendicular to it. Stated another way, the longitudinal axis of the needle is perpendicular to opposing membrane material in the transfer area, A, with open end 601 directly abutting (or at least in close proximity to) the membrane material. As a result, fluid flowing from the needle 510 need not make a 90° bend to be deposited on membrane 504. Instead, the fluid can flow directly onto the membrane 504 and be wicked on to the membrane material to a test area, T, covering opening 604. This enhances the transfer of fluid from the needle 510 to the membrane 504. Further, with this arrangement, the material of the membrane 504 can act as a filter to filter out undesirable blood cells or cell fragments which may, from time to time, be transferred through the needle 510 to the membrane 504. The transfer of blood cells or cell fragments onto the membrane 504 can also be reduced by providing a protein filter on the membrane in the region 610 (a filter area). Such a protein filter can be a physical filter or a filter composed of a binding agent (for example a chemical in that region to which blood, cell fragments, or other proteins may naturally attach to prevent further transfer of the proteins into the target, T, area of the membrane). Examples of such binding agents are diethanolamine, carboxymethylcellulose, quaternary amines, and anti-RBC antibodies.

Having disclosed the present invention and a preferred embodiment, it will be appreciated that modifications and equivalents of the disclosed concepts may readily occur to one skilled in the art. It is intended that such modifications and equivalents shall be included within the scope of the claims which are appended hereto.

What is claimed is:

1. A method for collecting body fluid from the skin, said method comprising:

providing a sampling device comprising a base, a sample needle having an axis and a distal end, a first pressure surface distinct from said base and at least partially surrounding said needle in spaced relation thereto, wherein said needle and said first pressure surface are movable relative to one another and to said base along a path of travel generally parallel to said axis with said needle, and a second pressure surface at least partially surrounding said needle, the second pressure surface fixed relative to said needle and movable relative to said base; said second pressure surface axially spaced from said distal end of said needle by a distance approximating a desired penetration of said needle into said skin;

urging said first pressure surface against said skin with a force sufficient to define a pressurized zone of interstitial fluid opposing said needle; and biasing said first pressure surface to a position wherein said distal end of said needle is recessed behind said first pressure surface.

2. The method of claim 1, further comprising:

urging said needle and said second pressure surface distally of said first pressure surface wherein the needle penetrates the skin until said second pressure surface is caused to contact the skin.

3. The method of claim 2, further comprising biasing the second pressure surface to a position wherein said first pressure surface is recessed behind said second pressure surface.

4. The method of claim 2, wherein said first pressure surface is initially biased with about three to about four pounds per inch and said second pressure surface is initially biased with about one to about two pounds per inch.

5. The method of claim 1, further comprising collecting body fluid within the skin and transporting it through the needle to a testing area.

* * * * *